(12) United States Patent
Bornstein

(10) Patent No.: US 9,517,355 B2
(45) Date of Patent: Dec. 13, 2016

(54) NEAR-INFRARED ENHANCEMENT OF CIRCADIAN AND ULTRADIAN SPATIOTEMPORAL CELLULAR COORDINATION

(71) Applicant: NOMIR MEDICAL TECHNOLOGIES, INC., Woodmere, NY (US)

(72) Inventor: Eric Bornstein, Woodmere, NY (US)

(73) Assignee: NOMIR MEDICAL TECHNOLOGIES, INC., Woodmere, NY (US)

(*) Notice: Subject to any disclaimer, the term of this patent is extended or adjusted under 35 U.S.C. 154(b) by 372 days.

(21) Appl. No.: 14/455,497

(22) Filed: Aug. 8, 2014

(65) Prior Publication Data

US 2015/0025599 A1    Jan. 22, 2015

Related U.S. Application Data

(63) Continuation-in-part of application No. PCT/US2013/025624, filed on Feb. 11, 2013.

(60) Provisional application No. 61/739,331, filed on Dec. 19, 2012, provisional application No. 61/637,681, filed on Apr. 24, 2012, provisional application No. 61/597,497, filed on Feb. 10, 2012.

(51) Int. Cl.
*A61N 5/06* (2006.01)

(52) U.S. Cl.
CPC ..... *A61N 5/0613* (2013.01); *A61N 2005/0626* (2013.01); *A61N 2005/0659* (2013.01)

(58) Field of Classification Search
CPC .............. A61N 2005/0626; A61N 2005/0659; A61N 5/0613
See application file for complete search history.

(56) References Cited

U.S. PATENT DOCUMENTS

| | | |
|---|---|---|
| 5,860,967 A | 1/1999 | Zavislan et al. |
| 2004/0073278 A1 | 4/2004 | Pachys |
| 2007/0197884 A1 | 8/2007 | Bornstein |
| 2008/0160539 A1 | 7/2008 | Murphy et al. |
| 2010/0285031 A1 | 11/2010 | Sukumar et al. |

FOREIGN PATENT DOCUMENTS

WO    2009103165 A1    8/2009

OTHER PUBLICATIONS

International Search Report and written opinion for PCT/US13/25624, mailed on May 13, 2013.
Sukumaran, et al., "Circadian Rhythms in Gene Expression: Relationship to Physiology, Disease, Drug Disposition and Drug Action", Adv Drug Deily Rev, 62(9-10), pp. 904-917, (2010).

(Continued)

*Primary Examiner* — Gary Jackson
*Assistant Examiner* — Scott T Luan
(74) *Attorney, Agent, or Firm* — The Marbury Law Group, PLLC

(57) ABSTRACT

A method is disclosed of providing photo-chrono-therapy to a wound site in a human or animal subject, the method including: determining or receiving subject circadian and/or ultradian cycle information indicative of a biological rhythm(s) of the subject; and based on the subject cycle information, delivering a photo-chrono-dose of infrared treatment light to the wound site with wavelengths within at least one infrared wavelength range and having a dosimetry configured to promote healing at the wound site.

20 Claims, 15 Drawing Sheets

(56) References Cited

OTHER PUBLICATIONS

Toyokawa, et al., "Promotove Effects of Far-Infrared Ray on Full-Thickness Skin Wound Healing in Rats", Soc Experimental Biology and Medicine, pp. 724-729, (2004).
Tsai, et al., "Cell Cycle-Dependence of HL-60 Cell Deformability", Biophys Journal, vol. 70, pp. 2023-2029, (Apr. 1996).
International Preliminary Report on Patentability from the International Bureau of WIPO for International Application No. PCT/US2013/025624 dated Aug. 12, 2014.
Sheetz, et al., Abstract of "Cell Migration as a Five-Step Cycle", Department of Cell Biology, Biochemical Society Symposium, p. 1, (1999).
Gachon, et al., "The role of circadian timing system on drug metabolism and detoxification", Expert opinion on drug metabolism & toxicology 7.2, pp. 147-158, (2011).
Bartness, et al., "SCN efferents to peripheral tissues: Implications for biological rhythms", Journal of Biological Rhythms, vol. 16, No. 2, pp. 196-204, (2001).
Gov, N. "Membrane undulations driven by force fluctuations of active proteins." Physical Review Letters, PRL 93(26), pp. 2681041 to 268104-4, (2004).
Krol, et al., "Local mechanical oscillations of the cell surface within the range 0.2-30 Hz." European Biophysics Journal 19.2, pp. 93-99, (1990).
Sandu, et al., "Human skin keratinocytes, melanocytes, and fibroblasts contain distinct circadian clock machineries." Cellular and Molecular Life Sciences pp. 1-11, (2012).
Albrecht-Buehler, Guenter. "Is Cytoplasm Intelligent Too?." Cell and Muscle Motility, 6, pp. 1-21, (1985).
Peplow, et al., "Laser Photobiomodulation of Proliferation of Cells in Culture: A Review of Human and Animal Studies." Photomedicine and Laser Surgery, vol. 28, Supplement 1, pp. S-3 to S-40, (2010).
Takei, et al., "Effect of Strain on Human Keratinocytes In Vitro", Journal of Cellular Physiology, 173, pp. 64-72, (1997).
Ezure, et al., "Adiponectin and leptin up-regulate extracellular matrix production by dermal fibroblasts", BioFactors 31, pp. 229-236, (2007).
Iwasaki, et al., "Cell-Cycle Dependent Invasion In Vitro by Rat Ascites Hepatoma Cells", Int. J. Cancer, 63,pp. 282-287, (1995).
Converse, et al., "Comparison of Wound Healing Using the CO2 Laser at 10.6 μm and 9.55 μm" The Laryngoscope 111.7, pp. 1231-1236, (Jul. 2011).
Knies, et al., "Mechanical stretch induces clustering of beta1-integrins and facilitates adhesion", Experimental Dermatology, 15, pp. 347-355, (2006).
Alt, et al., "Patterns of spontaneous motility in videomicrographs of human epidermal keratinocytes (HEK)", Biochem. Cell Biol. 73, pp. 441-459, (1995).
Ingber, "Tensegrity: the Architectural Basis of Cellular Mechanotransduction", Annu. Rev. Physiol., 59, pp. 575-599, (1997).
Peura, et al., "Improved skin wound epithelialization by topical delivery of soluble factors from fibroblast aggregates", Burns 38, pp. 541-550, (2012).
Ratner, et al., "Motility of murine lymphocytes during transit through cell cycle, Analysis by a new in vitro assay", The Journal of Immunology, vol. 140, No. 2, pp. 583-588, (Jan. 15, 1988).
Perozo et al., "Open channel structure of MscL and the gating mechanism of mechanosensitive channels", Nature, vol. 418, pp. 942-948, (2002).
Licinio, et al., "Human leptin levels are pulsatile and inversely related to pituitary-adrenal function", Nature Medicine, vol. 3, No. 5, pp. 575-579, (May 1997).
Wang, et al., "Mechanotransduction at a distance: mechanically coupling the extracellular matrix with the nucleus", Nature Reviews Molecular Cell Biology, vol. 10, pp. 75-82, (Jan. 2009).
Perozo, et al., "Physical principles underlying the transduction of bilayer deformation forces during mechanosensitive channel gating", Nature Structural Biology, vol. 9, No. 9, pp. 696-703, (Sep. 2002).
Serebryakov, et al., "Medical applications of mid-IR lasers. Problems and prospects." Journal of Optical Technology 77.1, pp. 6-17, (Jan. 2010).
Sinha, et al. "Ultradian Oscillations of Leptin Secretion in Humans", Biochem Biophysical Research Communications, vol. 228, pp. 733-738, (1996).
Walmod, et al., "Cell-cycle-dependent regulation of cell motility and determination of the role of Rac1", Exp Cell Res 295, pp. 407-420, (2004).
Alt, et al., "Cytoplasm dynamics and cell motion: two-phase flow models." Mathematical biosciences 156.1, pp. 207-228, (1999).
Gelse, et al., "Collagens—structure, function, and biosynthesis." Advanced Drug Delivery Reviews, 55, pp. 1531-1546, (Jan. 20, 2003).
Reichelt, "Mechanotransduction of keratinocytes in culture and in the epidermis", European Journal of Cell Biology 86, pp. 807-816, (2007).
Wang, et al., "Mechanobiology of Adult and Stem Cells", International Review of Cellular and Molecular Biology, vol. 271, pp. 301-346, (2008).
Lin, et al., "Nonequilibrium Membrane Fluctuations Driven by Active Proteins." The Journal of Chemical Physics, 124 pp. 1-16, (2004).
AlGhamdi, et al., "Low-level laser therapy: a useful technique for enhancing the proliferation of various cultured cells" Lasers in medical science 27.1, pp. 237-249, (Jan. 5, 2011).
Lévi, et al., "Circadian Timing in Cancer Treatments." Annual Review of Pharmacology and Toxicology 50, pp. 377-421, (2010).
Glasow, et al., "Expression of Leptin (Ob) and Leptin Receptor (Ob-R) in Human Fibroblasts: Regulation of Leptin Secretion by Insulin", The Journal of Clinical Endocrinology & Metabolism, 86(9), pp. 4472-4479, (2001).
Ahmad, et al., "Circadian and Ultradian Rhythm and Leptin Pulsatility in Adult GH Deficiency: Effects of GH Replacement", Journal of Clinical Endocrinology & Metabolism 86(8), pp. 3499-3506, (2001).
Albrecht-Buehler, "Surface Extensions of 3T3 Cells Towards Distant Infrared Light Sources." The Journal of Cell Biology, vol. 114, No. 3, pp. 493-502, (Aug. 1991).
Brown, et al., "The Period Length of Fibroblast Circadian Gene Expression Varies Widely Among Human Individuals", PLoS Biology, vol. 3, Issue 10, pp. 1813-1818, (Oct. 2005).
Driscoll, et al., "Cell Shape Dynamics: From Waves to Migration." PLoS Computational Biology, vol. 8, Issue 3, e1002392, pp. 1-10, (Mar. 2012).
Duffy, et al., "Effect of Light on Human Circadian Physiology", Sleep Med Clin. 4(2), pp. 165-177, (2009).
Frank et al., "Leptin enhances wound re-epithelialization and constitutes a direct function of leptin in skin repair", J. Clin. Invest. 106, pp. 501-509, (2000).
Giannone, et al., "Periodic Lamellipodial Contractions Correlate with Rearward Actin Waves", Cell, vol. 116, pp. 431-443, (Feb. 6, 2004).
Giannone, et al., "Lamellipodial Actin Mechanically Links Myosin Activity with Adhesion-Site Formation",Cell, vol. 128, pp. 561-575, (Feb. 9, 2007).
Giet, et al., "Increased binding and defective migration across fibronectin of cycling hematopoietic progenitor cells", Blood, vol. 99, No. 6, pp. 2023-2031, (Mar. 2002).
Gov, et al., "Red Blood Cell Shape and Fluctuations: Cytoskeleton Confinement and ATP Activity." Journal of Biological Physics 31, pp. 453-464, (2005).
Gov, et al., "Dynamics of Membranes Driven by Actin Polymerization." Biophysical Journal, vol. 90, pp. 454-469, (Jan. 2006).
Huang, et al., "Biphasic Dose Response in Low Level Light Therapy" Dose-Response 7.4, pp. 358-383, (2009).
Hutson, et al., "Advances in the Physical Understanding of Laser Surgery at 6.45 Microns", Proceedings of the Intl. Free Electron Laser Conf., pp. 648-653, (2004).
Ingber, "Cellular mechanotransduction: putting all the pieces together again", The Faseb Journal, pp. 811-827, (2006).

(56) References Cited

OTHER PUBLICATIONS

Murad, et al., "Leptin is an autocrine/paracrine regulator of wound healing", The FASEB Journal, pp. 1895-1909, (Aug. 15, 2003).
Nteleki, et al., "The use of phototherapy in the treatment of diabetic ulcers." Journal of Endocrinology, Metabolism and Diabetes of South Africa, vol. 17, No. 3, pp. 128-132, (2012).
Orr, et al., "Mechanisms of Mechanotransduction", Developmental Cell, vol. 10, pp. 11-20, (Jan. 2006).
Reno, et al., "Mechanical stretching modulates growth direction and MMP-9 release in human keratinocyte monolayer", Cell Adhesion and Migration, 3:3, pp. 239-242, (2009).
Sancar, et al., "Circadian Clock Control of the Cellular Response to DNA Damage", FEBS Letters 584(12), pp. 2618-2625, (2010).

1) Convex Axicon Lens

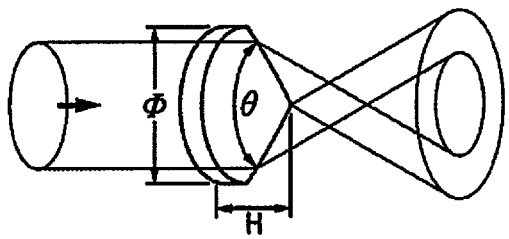

| | |
|---|---|
| Material: | Optical Glass and Fused Silica |
| $\Phi$: | 2~150nm ±0.02nm≤ |
| H: | ≤70nm ±0.05nm≤ |
| $\theta$: | 30~170° 6minutes≤ |
| Surface Accuracy of Axicon surface: | Power 8 fringes |
| Surface Accuracy of plane surface: | $\lambda/10$ |
| S/D: | 10/5 |

2) Concave Axicon Lens

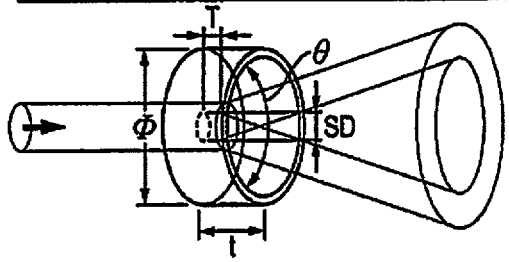

| | |
|---|---|
| Material: | Optical Glass and Fused Silica |
| $\Phi$: | 10~120nm ±0.02nm≤ |
| H: | ≤70nm ±0.05nm≤ |
| $\theta$: | 60~170° 20minutes≤ |
| Surface Accuracy of Axicon surface: | Power 8 fringes |
| Surface Accuracy of plane surface: | $\lambda/10$ |
| S/D: | 10/5 |

3) Meniscus Axicon Lens

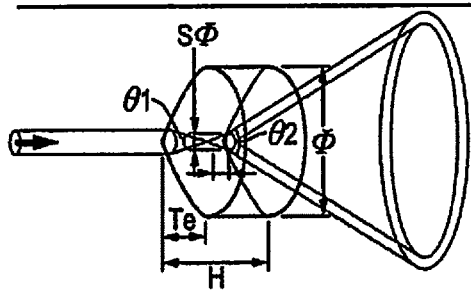

| | |
|---|---|
| Material: | Optical Glass and Fused Silica |
| $\Phi$: | 6~120nm ±0.02nm≤ |
| H: | ≤70nm ±0.05nm≤ |
| $\theta$ Cx: | 30~170° 6minutes≤ |
| $\theta$ Cc: | 60~170° 20minutes≤ |
| Surface Accuracy of Axicon surface: | Power 8 fringes |
| Surface Accuracy of plane surface: | $\lambda/10$ |
| S/D: | 10/5 |

4) Surgical Rod

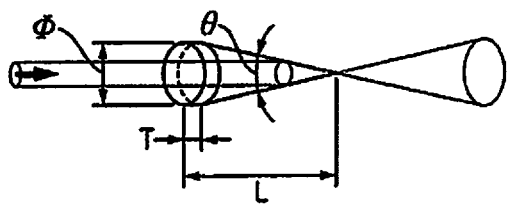

| | |
|---|---|
| Material: | Optical Glass, Fused Silica and Sapphire |
| $\Phi$: | 1.7~10nm ±0.05nm≤ |
| Length: | ≤20nm ±0.05nm≤ |
| $\theta$: | 10° 6minutes≤ |
| Surface Accuracy of Axicon surface: | Power 8 fringes |
| Surface Accuracy of plane surface: | $\lambda/10$ |
| S/D: | 10/5 |

Fig. 6A $$R_0 = R.O.C.\left(90° - \frac{\theta}{2}\right)$$
$$2\beta = 2\left(90° - \frac{\theta}{2}\right)$$

| Time post seeding (hours) | Doubling Time (hours) | | |
| --- | --- | --- | --- |
| | 0ng/ml Hydrocortisone | 50ng/ml Hydrocortisone | 100ng/ml Hydrocortisone |
| 24 | 17.78 | 17.63 | 45.58 |
| 48 | 27.77 | 25.61 | 42.73 |
| 72 | 23.21 | 27.46 | 38.51 |

Fig. 11

| Cell Type | Calculated Period Length (hours) | | | | | | |
|---|---|---|---|---|---|---|---|
| | median (midpoint) | median (lower limit) | median (upper limit) | mean (midpoint) | mean (lower limit) | mean (upper limit) | var |
| Human fibroblasts (Per2::luc) | 19.44 | 19.37 | 19.51 | 19.47 | 19.40 | 19.54 | 333053.28 |
| Human fibroblasts (Per2::luc) | 24.32 | 24.23 | 24.41 | 24.62 | 24.53 | 24.71 | 1017847.02 |
| Human fibroblasts (Bmal1::luc) | 22.55 | 22.46 | 22.63 | 21.85 | 21.77 | 21.93 | 3712536.24 |

Fig. 12

NEAR-INFRARED ENHANCEMENT OF CIRCADIAN AND ULTRADIAN SPATIOTEMPORAL CELLULAR COORDINATION

CROSS REFERENCE TO RELATED APPLICATIONS

This application is a continuation in part of International Application No. PCT/US2013/025624, titled "NEAR-INFRARED ENHANCEMENT OF CIRCADIAN AND ULTRADIAN SPATIOTEMPORAL CELLULAR COORDINATION IN THE HUMAN INTEGUMENTARY SYSTEM," and filed Feb. 11, 2013 which in turn claims priority from U.S. Provisional Application 61/739,331, titled "Selective Re-Establishment of Ultradian Oscillations in Wounds to Accelerate Fibroblast and Keratinocyte Motility and Translation", filed Dec. 19, 2012, and U.S. Provisional Application 61/637,681, titled "Selective Re-Establishment of Ultradian Oscillations in Wounds to Accelerate Fibroblast and Keratinocyte Motility and Translation" filed Apr. 24, 2012, and U.S. Provisional Application 61/597,497, titled, "Wound Treatment Apparatus, System and Method", filed Feb. 10, 2012. The entire contents of each of the foregoing applications are incorporated herein by reference.

BACKGROUND

The following background section is presented for informational purposes only, and does not constitute an admission that any of the material presented in this section qualifies as prior art to the current application.

This disclosure relates to methods and systems for exploiting human circadian and ultradian control systems with different temporal and optical projections of selected wavelengths of infrared energy, specifically in and around the human integumentary system:

The present disclosure generally relates to methods and systems for exploiting human or animal circadian and ultradian control systems with different temporal and optimal projections of selected wavelengths of infrared energy in and around the human integumentary system. The science describing these devices and methods will be termed chrono-photo-biology by the current inventor. Human circadian control systems function as a result of a series of endogenous molecular clocks that govern 24-hour physiologic and cellular metabolic fluctuations. Ultradian control systems govern recurrent biological periods or cycles that are repeated throughout a 24-hour "circadian" day. These Circadian and ultradian fluctuations drive cellular metabolism, cell cycle events, angiogenesis, DNA repair, cellular apoptosis, immune functions and most other metabolic and physiologic systems in the human integumentary system.

On a cellular level, the circadian and ultradian clocks are coordinated by endogenous physiological rhythms, and work in a synchronous manner, so that specific spatiotemporal cellular events in the cell cycle such as quiescence and proliferation (mitosis) can be predicted in most tissues. With chrono-photo-biology, improved photobiologic treatment efficacy can be performed, when specifically titrated therapies are given in times of optimum tolerability, which can be predicted based on a patients endogenous circadian and ultradian rhythms. The recognition of this circadian and ultradian timing for hormonal and cell cycle regulation in the human integumentary system, and its exploitation as a method of augmenting photobiologic therapy, has the capacity to modify and vastly improve induced photobiologic effects. Positive cellular responses to phototherapy can increase many fold, in areas such as fibroblast and keratinocyte optically directed photo-taxis and cell translocation, wound healing, skin growth, local endogenous leptin secretion, and enhanced collagen deposition. The present invention particularly, relates to methods and systems for exploitation of human circadian and ultradian clocks, as a method of improving photobiologic therapy in and around the human integumentary system.

An abundance of studies spanning the past three decades have shown selected beneficial effects of various light therapies on human epidermal and dermal tissues. These positive effects have been described as the stimulation of DNA and RNA synthesis, promotion of cell adhesion, acceleration of wound healing, extracellular matrix proliferation, fibroblast collagen production, increased production of granulation tissue and reduction of the inflammatory response. While several of these different occurrences (and increased or decreased effects) have been researched in vitro and in vivo, to the applicant's knowledge there are no studies that have selectively researched the effect of light therapy, when tied to the inherent circadian and ultradian rhythms that govern human integumentary cells and their biochemistry and metabolism. Studies of various calibers, in the last three decades have instead focused largely on different "instruments and mechanisms of light therapy" to effect cellular signaling molecules such as ATP, cellular metabolites, and various forms of reactive oxygen species, all in the absence of cell cycle temporal data and components.

The vast majority of light therapy studies in the last three decades have focused on wound healing. These studies have generated a tremendous quantity of information concerning cellular proliferative effects, cell motility, and various stimulatory effects. However, it is rarely the case, that a given data set (form any in vitro or in vivo study) can be easily reproduced with a photo-therapy protocol or device. Many researchers have argued that the reason for this difficulty is that most studies do not adequately disclose one or more of the important parameters of the treatment such as (a) light output power, (b) irradiation treatment time, (c) irradiation spot size and/or (d) the degree of wavelength purity of the treatment device.

The present applicant has realized that the field of infrared phototherapy may be significantly advanced by study of the effects of infrared phototherapy from the perspective of the circadian and ultradian rhythms that govern the cells being treated in and around the human integumentary system. For example, in the plethora of studies that have been conducted looking for augmentation of fibroblast and keratinocyte motility, to the applicant's knowledge not a single one has described the therapy in temporal terms with respect to the G1/S phase of the 24-hour cell cycle. This would be vital information, as the G1/S phase (described below) is when human fibroblasts and keratinocytes have the greatest ability to express motility and translocate into a wound environment.

For the last 30 years, there has been a lack of appreciation of the spatiotemporal cellular coordination in the cell cycle when designing and performing infrared photo-therapy studies. This causes primary inaccuracies in data and results, as the capacity of cell motility and translocation is depressed at various times in the cell cycle, along with the fact that the majority of cellular energy and resources are being used for other vital processes like DNA replication and cytokinesis. These are not opportune times for infrared irradiation, if the effect that you desire is cell motility or collagen deposition.

Infrared irradiation at these times, would actually act as a chrono-disruptive force, and not as an additive benefit. As far as the applicant is aware, infrared circadian and ultradian spatiotemporal cellular coordination, which is described herein has hitherto never previously been proposed to augment or increase the potential benefits or inhibit potential detriments to performing photo-therapy (in vitro or in vivo) on human integumentary cells and tissues.

In some aspects, the present disclosure advantageously leverages the discovery that specific narrow wavelengths of infrared energy, delivered at the correct dose, are not the only vital parameters necessary to enable efficacious therapy. The present disclosure brings to bare devices and methods to (a) analyze and (b) produce photo-therapy at the proper circadian and ultradian spatiotemporal windows for desired events, along with the most efficacious dispersion of energy during cell cycle events.

Optically based infrared photo-therapy generated and delivered within specific ultradian and circadian parameters based on a patient's own endogenous temporal rhythms has never been previously envisioned or studied in the history of photo-therapy. Merely it has been known that circadian and ultradian rhythms exist, and that their properties and repeating nature govern a plethora of cellular events.

As an example of this omission of circadian and ultradian spatiotemporal understanding can be seen in the recent detailed and comprehensive laser reviews (2010 Peplow et al and 2012 AlGhamdi et al) entitled "Laser photo-biomodulation of proliferation of cells in culture: a review of human and animal studies." and "Low-level laser therapy: a useful technique for enhancing the proliferation of various cultured cells". Therein, where approximately 200 articles were reviewed, only three mentions could be found of any researchers that temporally synchronized the cell cycle of the cells being studied. Without this basic measure as a control factor, for whether the cells being studied were in a specific point of interphase or mitosis, there can be little hope of duplicating and reproducing data and results. Furthermore, even in those few cases where some level synchronization was provided, no effort was made to correlate the application of treatment to selected phase in the cell cycle.

In another example, (Bahle 2012) writing a detailed review of phototherapy for Diabetic ulcers, did not list a single reference to circadian and ultradian spatiotemporal coordination with the photo-therapy or irradiation, from any studies in the review.

In another example (Huang 2009) writing a detailed review of Low Level Light therapy, with 111 references, did not mention once the circadian and ultradian spatiotemporal stage of the cell cycle, in the cells being tested and results being reported. There was no mention if the cells were at specific point of interphase or mitosis, and yet remarkably, with this missing cell cycle information, Huang et al concludes that, "In general, fluences of red or NIR as low as 3 or 5 J/cm^2 will be beneficial in vivo, but a large dose like 50 or 100 J/cm^2 will lose the beneficial effect and may even become detrimental" Statements like this are widespread throughout the literature, but cannot be supported or reproduced in a meaningful way, as there is no correlation to the spatio-temporal phase of the cell cycle that these cells were in when they were irradiated. Hence, the data cannot be reproduced, and there is no control to see if in fact the photo-therapy was beneficial or chrono-disruptive, based on where in the cell cycle the cells were temporally at the time of irradiation.

SUMMARY

The objectives of the present disclosure are based in the new science of photo-chrono-biology and photo-chrono-therapeutics. Photo-chrono-therapeutics is a new discipline created by the present inventor, to improve the tolerability and efficacy of photobiologic therapy. This is accomplished by the supervision and management of information concerning circadian and ultradian spatiotemporal cellular events in the human integumentary system, with specific targeted light based therapies, according to a patient's own circadian and ultradian rhythms. Targeted photo-chrono-therapeutics makes use of the periodic nature of the circadian time organization by the 24-hour day and endogenous ultradian rhythms and allows for the critical prediction of vital cellular peaks and troughs of biochemical rhythms in the human integumentary system.

These peaks deal with temporal and hormonal regulation of the (1) rest phase, (2) growth phase and (3) mitotic phase of cellular energetics, enzyme production and mitosis. With sufficient temporal adjustment to the frequency and administration of photobiologic therapy, so as to coincide properly with a patient's circadian rhythms and ultradian rhythms, photo-chrono-therapy can be achieved. This will improve therapeutic outcomes in patients receiving photo-therapy.

In one aspect, a method is disclosed of providing photo-chrono-therapy to a wound site in a human or animal subject, the method including: determining or receiving subject circadian and/or ultradian cycle information indicative of a biological rhytlun(s) of the subject; and based on the subject cycle information, delivering a photo-chrono-dose of infrared treatment light to the wound site with wavelengths within at least one infrared wavelength range and having a dosimetry configured to promote healing at the wound site.

In some embodiments, the subject cycle information includes circadian information indicative of a circadian rhythm of the subject. Some embodiments include delivering the photo-chrono-dose includes delivering the treatment light at a time corresponding to one or more selected phases in a cell-cycle of the subject based on the circadian information. In some embodiments, the one or more selected phases include a G1 or early S-phase of the cell-cycle.

In some embodiments, the wound site includes an internal and an external peripheral portion having a wound margin (the internal peripheral portion being located on the side of the margin towards the wound, and the external peripheral portion on the side of the margin away from the wound) and a central portion. In some embodiments, delivering a photo-chrono-dose of infrared treatment light to the wound site includes preferentially delivering light to either or both of the peripheral portions of the wound singly or simultaneously.

Some embodiments include stimulating migration of eukaryotic cells from the peripheral portion of the wound site to the central portion of the wound site. In some embodiments, the eukaryotic cells include at least one of fibroblasts and keratinocytes. In some embodiments, stimulating migration of eukaryotic cells includes generating spatio-temporal photo-taxis in the eukaryotic cells. In some embodiments, generating spatio-temporal photo-taxis in the eukaryotic cells includes causing optically mediated mechanotransduction at cell membranes to stimulate directed lamellopod or pseudopod creation in the cells. In some embodiments, the optically mediated mechanotransduction causes forces at the cell membrane that reinforce endogenous membrane waves in the cells.

Some embodiments include preferentially delivering light to the internal or external peripheral portion includes delivering the light with a substantially annular spatial distribution. In some embodiments, the light with a substantially annular spatial distribution includes delivering the light as a ring of spots at the wound cite.

In some embodiments, the subject cycle information includes ultradian information indicative of an ultradian rhythm of the subject, and further including modulating the treatment light delivered to the wound site based on the ultradian information. In some embodiments, the ultradian information includes information indicative of a pulse or heartbeat in the subject.

Some embodiments include receiving at least one sensor signal indicative of the ultradian information. In some embodiments, the sensor signal includes a pulse oximeter signal or an electrocardiogram signal.

In some embodiments, delivering the photo-chrono-dose of infrared treatment light includes: generating near-infrared optical radiation with wavelengths within a first wavelength range of 850 nm to 900 nm or a second wavelength range of 910 nm to 950 nm; and delivering the near-infrared optical radiation to the wound site with a power density at the treatment sight in the range of 0.015-1.0 W/cm^2 and an energy density in the range of 0.5-3500 J/cm^2.

In some embodiments, the near-infrared optical radiation in the first wavelength range is within the range of 865 nm to 875 nm. In some embodiments, the near-infrared optical radiation in the second wavelength range is within the range of 925 nm to 935 nm. In some embodiments, the near-infrared optical radiation includes radiation in the first and second wavelength ranges.

Some embodiments include applying the near infrared optical radiation to stimulate leptin production from adipose tissue in the external periphery of the wound site.

Some embodiments include stimulating collagen synthesis at the wound site by delivering mid-infrared optical radiation to the wound site. In some embodiments, delivering mid-infrared optical radiation to the wound site includes: generating mid-infrared optical radiation substantially in a third wavelength range of 6.35 microns to 6.55 microns; and delivering the mid-infrared optical radiation to the wound site with a power density at the treatment sight in the range of 0.01-1.0 W/cm^2 and an energy density in the range of 0.5-3500 J/cm^2. In some embodiments, the mid-infrared optical radiation in the third wavelength range is within the range of 6.44 nm to 6.46 nm. In some embodiments, generating mid-infrared optical radiation includes using a quantum cascade laser to produce the mid-infrared optical radiation.

In some embodiments, the wound site corresponds to an intentionally created wound. Some embodiments include intentionally creating the wound at the wound site. In some embodiments, intentionally creating the wound at the wound site includes applying at least one from the list consisting of: a chemical peel, dermabrasion, photo-rejuvenation, fractional laser therapy and laser resurfacing.

Some embodiments improving at least one of the skin thickness, smoothness, and strength in a healed wound at the wound cite, e.g., relative to a wound healed using only endogenous processes or otherwise in the absence of photo-chrono-therapy as described above.

Some embodiments include delivering the mid-infrared light to a central portion of the wound site to which cell migration has previously been stimulated using near-infrared light.

Some embodiments include delivering the mid-infrared light to the central portion of the wound site includes delivering the mid-infrared light with a substantially top-hat intensity distribution.

In another aspect, a system is disclosed for providing photo-chrono-therapy to a wound site in a human or animal subject, the system including: one or more sources of infrared optical treatment light; an optical output device configured to receive light output by the sources of optical treatment light and transmit the light to a delivery device for delivery to the wound site; and a processor operatively coupled to the sources of optical treatment. In some embodiments, the processor is configured to determine or receive subject cycle information indicative of a biological rhythm of the subject; and based on the subject cycle information, control the sources to deliver a photo-crono-dose of infrared treatment light to the wound site with wavelengths within at least one wavelength range and having a dosimetry configured to promote healing at the wound cite.

In some embodiments, the subject cycle information includes circadian information indicative of a circadian rhythm of the subject. In some embodiments, the processor is configured to control the sources deliver treatment light at a time corresponding to one or more selected phases in a circadian cycle of the subject based on the circadian information. In some embodiments, the one or more selected phases include a G1 or early S1 phase of the cell cycle of fibroblasts or keratinocytes.

In some embodiments, the wound site includes an internal and an external peripheral portion having a wound margin (the internal peripheral portion being located on the side of the margin towards the wound, and the external peripheral portion on the side of the margin away from the wound) and a central portion. In some embodiments, the delivery device is configured to preferentially deliver light to either the internal or external peripheral portion.

In some embodiments, the delivery device is configured to deliver light to the wound site with a substantially annular spatial distribution. In some embodiments, the delivery device is configured to deliver light to the wound site as a ring of spots. In some embodiments, the delivery device includes an axicon lense.

In some embodiments, all or a portion of the delivery device is connected to or incorporated in structure to be applied to or worn by the patient. In some embodiments, the structure includes at least one from the list consisting of: a bandage, a dressing, an article of clothing, or a medical support. In some embodiments, the delivery device includes a bandage having a plurality of light sources distributed in a pattern corresponding to a peripheral portion of the wound site including the wound margin.

Some embodiments include the delivery device.

In some embodiments, the subject cycle information includes ultradian information indicative of an ultradian rhythm of the subject. In some embodiments, the processor is configured to modulate the treatment light delivered to the wound site from the sources based on the ultradian information.

In some embodiments, the ultradian information includes information indicative of a pulse in the subject.

In some embodiments, the processor is configured to receive at least one sensor signal from a least one sensor indicative of the subject cycle information.

In some embodiments, the at least one sensor includes a first sensor configured to determine information indicative of an circadian rhythm and a second sensor configured to determine information indicative of a ultradian rhythm.

In some embodiments, the sensor includes at least one from the list consisting of: a pulse oximeter; an electrocardiogram, a blood pressure sensor, a thermometer, and an electroencephalography sensor.

Some embodiments include at least one of: a first near infrared optical source configured to generate near-infrared optical radiation with wavelengths within a first wavelength range of 850 nm to 900 nm. and a second near infrared optical source configured to generate near-infrared optical radiation with wavelengths within a second wavelength range of 910 to 950 nm. In some embodiments, the system is configured to deliver the near-infrared optical radiation from the sources to the wound site with a power density at the treatment sight in the range of 0.015-1.0 W/cm^2 and an energy density in the range of 0.5-3500 J/cm^2. In some embodiments, the near-infrared optical radiation in the first wavelength range is within the range of 865 nm to 875 nm. In some embodiments, the near-infrared optical radiation in the second wavelength range is within the range of 925 nm to 935 nm. Some embodiments include both the first and the second near infrared optical sources.

In some embodiments, the delivery device is configured to deliver light from the near-infrared optical sources to the wound site with a selected spatial pattern, and with substantially uniform intensity within the pattern.

In some embodiments, the near-infrared optical sources include a light emitting diode or a diode laser.

In some embodiments, the one or more optical sources include: a mid-infrared optical source configured to generate mid-infrared optical radiation substantially in a third wavelength range of 6.35 microns to 6.55 microns. In some embodiments, the system is configured to deliver the mid-infrared optical radiation to the wound site with a power density at the treatment sight in the range of 0.015-1.0 W/cm^2 and an energy density in the range of 0.5-3500 J/cm^2. In some embodiments, the mid-infrared optical radiation in the third wavelength range is within the range of 6.44 nm to 6.46 nm. In some embodiments, the mid-infrared optical source includes a quantum cascade laser.

In some embodiments, the delivery device is configured to deliver the mid-infrared optical radiation to a central portion of the wound site. In some embodiments, the delivery device is configured to deliver the mid-infrared optical radiation to a central portion of the wound site with a substantially top-hat intensity distribution.

Some embodiments include an aesthetic therapy module configured to intentionally create the wound at the wound site. In some embodiments, the aesthetic therapy module includes: a chemical peel module, a dermabrasion module, a photorejuvenation module, and a laser resurfacing and/or fractional laser module.

In some embodiments, the system in configured to improve at least one of the skin thickness, smoothness, and strength in a healed wound at the wound cite, e.g., relative to a wound healed using only endogenous processes or otherwise in the absence of photo-chrono-therapy as described above.

Various embodiments may use any of the above described elements alone or in any suitable combination.

BRIEF DESCRIPTION OF THE DRAWINGS

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. Where applicable, the same reference numbers are used throughout the drawings to refer to the same or like parts or features.

FIGS. 6A and 6B show schematic views for several optical elements for use with a delivery device in a photo-crono-therapy system.

FIG. 7B shows the device illuminated.

FIG. 9A shows a plot of activation energy versus reaction coordinate in the absence of the infrared light. FIG. 9B shows a plot of activation energy versus reaction coordinate in the presence of the infrared light.

FIG. 11 is a chart showing the results of human Keratinocyte and fibroblast circadian tests.

FIG. 12 is a chart showing the results of leptin analysis for irradiation of human adipocytes.

DETAILED DESCRIPTION

Figure 1A:
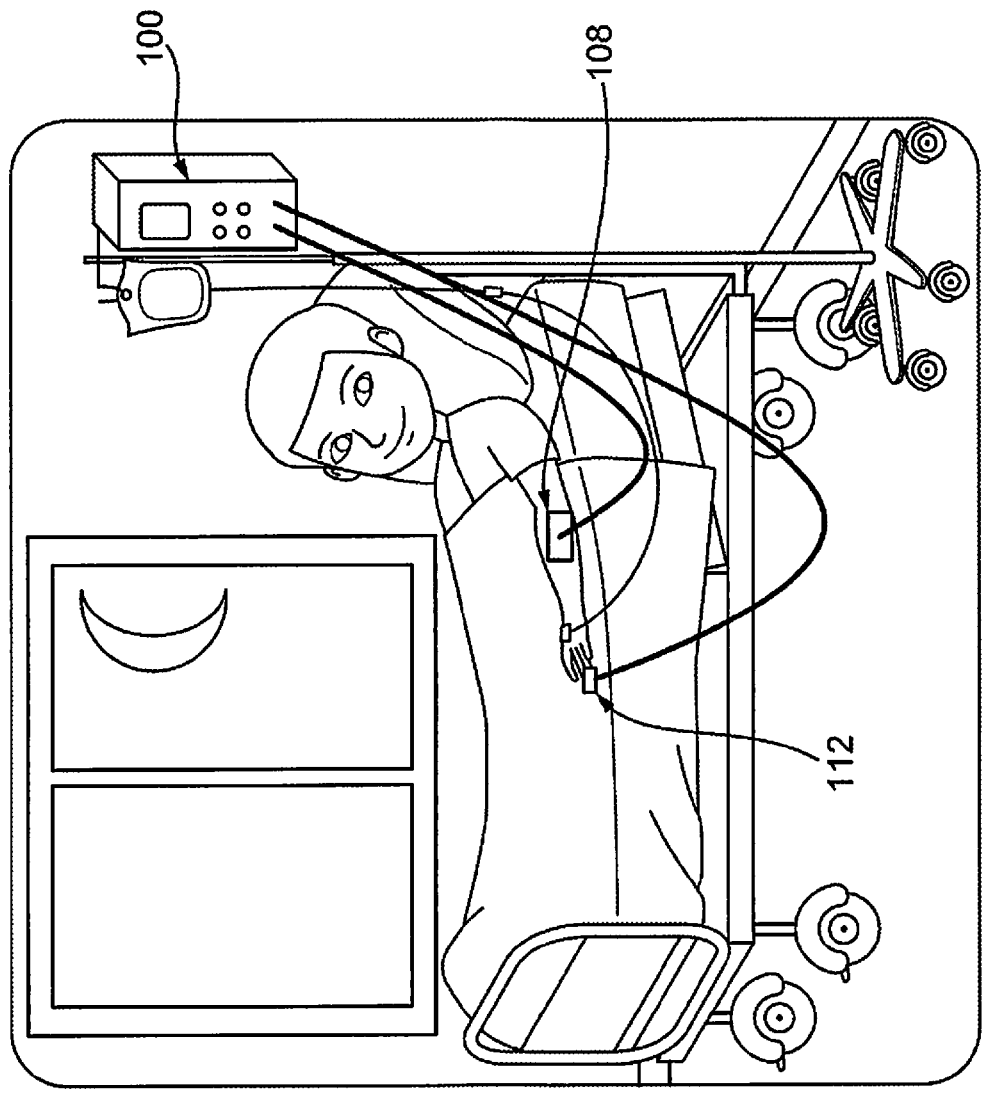
FIG. 1A is an illustration of photo-crono-therapy system.

The definitions of terms used herein are meant to incorporate the present state-of-the-art definitions recognized for each term in the fields of photobiology, circadian science, and molecular biology and to create new terms when necessary to adequately describe embodiments of the inventions disclosed herein. Where appropriate, exemplification is provided.

The definitions apply to the terms as they are used throughout this specification, unless otherwise limited in specific instances, either individually or as part of a larger group. In general, all technical and scientific terms used herein have the same meaning as commonly understood to one of ordinary skill in the art to which this invention belongs, unless clearly indicated otherwise. For clarification, listed below are certain definitions for certain terms used herein are novel, and are used to describe the present invention.

As used herein the term "chrono-choto-biology" denotes the exploitation of Circadian and Ultradian rythms on a Physiologic and/or cellular level in an organism to improve photo-therapeutic outcomes of treatment.

As used herein, the term photo-chrono-tolerance is the ability to irradiate a target tissue with infrared light at specific wavelengths at optimal circadian and/or ultradian times in the cell cycle, to allow for improved or even maximum tolerance of the energy, so as to not inhibit events such as motility and or mitosis, depending on the outcome that is desired.

As used herein, photo-chrono-modulation is the ability to alter dosimetry and time of target tissue irradiation with infrared light at specific wavelengths at advantageous or even optimal circadian and/or ultradian times in the cell cycle, to allow for maximum tolerance and therapeutic value of the energy.

As used herein photo-chrono-efficacy is the enhanced therapeutic effect that is seen from photo-therapy with infrared light at specific wavelengths at advantageous or even optimal circadian and/or ultradian times in the cell cycle.

As used herein photo-chrono-dose is the correct calculated dose of infrared energy that is given for photo-therapy with infrared light at specific wavelengths at optimal circadian and/or ultradian times in the cell cycle.

As used herein the term "Biological rhythm" denotes a self-sustained and endogenous biological oscillation As used herein the term "Circadian" denotes a biological rhythm with about a one day period (circa, about; dies, day). To be termed a "Circadian rhythm" the regularity of the biological event should generally meet the following criteria:
1. The rhythms repeat once a day, within a 24-hour period.
2. The rhythms in cells (and the organism) are endogenous and will persist in the absence of external cues. The rhythm persists in constant conditions with a period of about 24 hours.
3. The rhythms are entrainable, meaning that they can be adjusted to match local time, through exposure to external stimuli (such as light and heat).
4. The rhythms maintain circadian periodicity over a range of physiological temperatures.

As used herein the term "Circadian timing system (CTS)" denotes a biological system that generates ~24 hour rhythms in cell and organism and physiology and adjusts them to environmental cycles.

As used herein the term Ultradian rhythm refers to recurrent biological periods or cycles that are repeated throughout a 24-hour "circadian" day. Some examples of an ultradian rhythm are release of some hormones, heart rate, bowel activity, thermoregulation, REM sleep cycles, and stimulation and inhibition of appetite.

As used herein the term "Period" denotes a cycle duration of a self-sustained and endogenous biological oscillation.

As used herein, the term chrono-disruption refers to a circadian or ultradian rhythm that has become desynchronized, and is therefore having adverse effects on cellular health and the health of the organism.

As used herein, the term chronotype refers to a characteristic of human beings, that reflects at what time of the day physical functions such as hormone level, body temperature, eating and sleeping are active and occur. This phenomenon is commonly reduced to sleeping habits describing morning people (those who wake up early) and evening people (those who are most alert in the late evening and go to bed late).

As used herein, the term integumentary system refers to the organ system that protects the body from damage, containing the skin and all of its appendages (e.g., hair, finger nails, and toe nails). The integumentary system is the largest organ system in the body, and generally covers 1.5-2 m² of surface area.

The human skin is composed of 3 major layers of tissue: the epidermis; dermis; and hypodermis. The epidermis is the outermost layer. The dermis is the next layer, and comprises two sub sections, the papillary and reticular layers, that contain connective tissues, vessels, glands, hair follicles and roots, sensory nerve endings, and muscular tissue. The third and deepest layer is the hypodermis, which is primarily made up of adipose tissue. Significant amounts of collagen bundles anchor the dermis to the hypodermis in a configuration that allows most of the skin to freely move over the deeper tissue layers.

As used herein, the term epidermis refers to the outermost layers of the skin, that forms a protective barrier over the surface of the body, and is a stratified squamous epithelium. It is composed of proliferating basal and differentiated suprabasal keratinoicytes.

As used herein, the term epidermis can be sub-divided into the following layers, beginning with the outermost layer. (1) Stratum corneum, (2) Stratum lucidum (only in palms and soles), (3) Stratum granulosum (4) Stratum spinosum, (5) Stratum germinativum (also called the stratum basale).

Keratinocytes in the stratum basale multiply through mitosis and the daughter cells progress through layers changing shape and composition as they undergo multiple stages of cell differentiation. This ends with anucleated cells that become highly organized and form cellular junctions (desmosomes). These cells secrete keratin proteins and lipids that contribute to the formation of an extracellular matrix and provides substantial mechanical strength to the skin. These same keratinocytes from the stratum corneum continually shed from the surface of the skin (desquamation). The epidermis does not contain blood vessels, and cells in the deeper layers are nourished by diffusion from capillaries that extend into the upper layers of the dermis.

As used herein the term basement membrane describes the thin sheet of fibers that separate the epidermis and dermis. The basement membrane has, many functions including control of cellular and molecular traffic between the dermis and epidermis.

As used herein the term dermis refers to the layer of skin underneath the epidermis and is made up of connective tissue. The dermis affords strength and elasticity to the skin through the extracellular matrix that is composed of collagen fibrils, microfibrils, and elastic fibers, embedded in proteoglycans.

As used herein the term hypodermis refers to the layer below the dermis that is not part of the skin. The hypodermis attaches the skin to underlying bone and muscle as well as supplying the dermis with blood vessels and nerves. The hypodermis consists of loose connective tissue and elastin. The main cell types of the hypodermis are fibroblasts, macrophages and adipocytes (the hypodermis contains 50% of body fat). The hypodermis is also known as the subcutaneous tissue.

As used herein the term lamellipod refers to a cytoskeleton protein actin projection on the mobile edge of a cell that contains a quasi-two-dimensional actin mesh. The "structure" of a lamellipod propels the cell across a substrate. Lamellipodia are present at the front or leading edge of motile cells. Lamellipodia are thought to be the actual motor which will pull a cell forward during the process of motility or cell migration. Lamellipodia are also known to act as a steering devices for cells in the process of phototaxis or chemotaxis.

As used herein the term filopod (micro-spike) refers to slender cytoplasmic projection from a cell that extends beyond the leading edge of a lamellipod in migrating cells. Filopodia contain actin filaments cross-linked into bundles by actin-binding proteins, and form focal adhesions with the substratum and are thought to be involved in both sensation of phototropic and chemotropic cues, and that can result in changes in directed cellular locomotion. Filopodia are believed to also have roles in sensing, migration and cell-cell interactions. In humans, to close a wound, different growth factors stimulate the formation of filopodia in fibroblasts. These now "directed" fibroblasts migrate into the wound to assist in wound closure As used herein the term Pseudopod refers to a temporary projection of eukaryotic cells. Pseudopodia are capable of extending and contracting by the reversible assembly of the protein actin (in subunits) into microfilaments. Filaments near the cell's end (or tail) interact with myosin which will cause cellular contraction.

As used herein the term cell cycle, or cell-division cycle, refers to the series of events that take place in a cell that ultimately leads to its division and duplication into daughter cells. The cell cycle is a period of time in which a cell prepares for cell division, and then produces a new cell. In eukaryotic cells, the cell cycle is divided in two periods: Interphase and the Mitotic phase. The cell-cycle is a vital process by which skin, hair, blood cells and certain internal organs are renewed and regenerated. After cell division, each of the daughter cells begin the interphase of a new cell cycle.

As used herein the term G0 phase refers to the post-mitotic phase that is also referred to as the non-proliferative or quiescent phase of the cell cycle.

As used herein the term Interphase refers to the phase of the (mitotic) cell cycle in which the cell spends the majority of its time, and performs the majority of its purposes, which also includes preparation for cell division. The Interphase is composed of the following 3 sub-phases:

As used herein the term G1 phase refers to the first phase within interphase (if the cell does not go into G0 phase) from the end of the previous mitotic phase until the beginning of DNA synthesis. (G indicates gap). G1 is also called the growth phase. During G1, the majority of biosynthetic activities occurring in the cell (which had been considerably slowed down during mitotic phase), will resume at a high rate. During this time, the cell grows (to about double its original size)—more organelles are produced, increasing the volume of the cytoplasm. If the cell is not to divide again, it will remain in this phase.

As used herein the term S-phase (synthesis) refers to the phase that begins in the cell when DNA replication commences. When DNA replication is complete, all of the cells chromosomes will also have been replicated. Thus, during the S-phase, the amount of DNA in the cell will have doubled.

As used herein the term G2 phase refers to the third phase within interphase where the cell resumes its growth in preparation for division. When G2 is completed, the cell enters a relatively brief period of nuclear and cellular division, composed of mitosis and cytokinesis, respectively. After the successful completion of mitosis and cytokinesis, both resulting daughter cells re-enter G1 of interphase.

The M phase consists of nuclear division (karyokinesis). The M phase also consists of several distinct phases, sequentially known as prophase, metaphase, anaphase, and telophase. Cytokinesis is not part of mitosis but is the event that directly follows mitosis, in which cytoplasm of the cell is divided into two daughter cells.

The duration of time that a specific type of cell spends in interphase and in each stage of interphase is variable. Most adult human cells that are not in G0 phase spend approximately 20 hours in interphase.

As used herein, the term phototropic refers to directional growth in which the direction of growth is determined by the direction of the light source.

As used herein the term phototaxis refers to a kind of locomotory movement that occurs when a cell moves in response to the stimulus of light.

As used herein the term chemotaxis refers to a kind of locomotory movement that occurs when a cell moves in response to a chemical gradient.

As used herein, the term proteome refers to the entire set of proteins expressed by a genome, cell, or tissue at a certain time. More specifically, it is the set of expressed proteins in a given type of cell at a given time under defined conditions.

In embodiments described herein, understanding of the chrono-photo-biology of cells is used to produce advantageous effects, including improved healing of wounds. In various embodiments, a photo-chrono-dose of infrared light is applied to a subject (e.g., using a system of the type described with reference to FIGS. 1A-2 below) at controlled times and with controlled dosimetry informed by the biological cycles of the subject. For example, as detailed below, the phototherapy may be applied at specific times during a subject's circadian cycle to provide advantageous effects. The phototherapy may also by synched to shorted ultradian rhythms (e.g., by modulating the applied light based on the heartbeat or pulse of the subject) to provide additional benefits.

Many cellular, and molecular processes function temporally with 24-h cycles that are impelled by the light-dark cycle of day and night. These processes are controlled directly or indirectly by the central circadian clock, in the paired suprachiasmatic nuclei in the anterior part of the hypothalamus (in the brain). The central circadian clock receives direct input of light through the retino-hypothalamic tract, which in turn synchronizes the endogenous circadian clock to the daily light-dark cycle. The peripheral (tissue) clocks are also circadian oscillators that are controlled and coordinated by the central clock. (Duffy et al 2009, Bartness et al and 2001, Sukumaran et al 2010)[5,6,7]

Dermal and epidermal tissues are continuously interacting with the outside environment, and as such they are continuously exposed to foreign material and insults. Therefore, to maintain normal homeostasis and function, the human integumentary system undergoes constant repair and turnover. There is a continuous metabolic and cellular rebuilding of the extracellular and intracellular components of the skin through the cell cycle and mitosis, new whole cells are produced on a daily basis. The circadian and ultradian rhythms of integumentary tissues can be disrupted and altered by things like chronic sleep loss or sleep deprivation or systemic dysregulation and/or disease.

In dermal and epidermal tissues, circadian and ultradian oscillations in the expression of genes that are associated with (i) building the extracellular matrix, (ii) cytoskeleton construction and (iii) cell cycle quiescence, suggest that repair and cellular turnover of important cellular components are under the spatio-temporal regulation of the molecular clock, and tied to the circadian rhythm.

Recent scientific research has identified a series of molecular triggers and events that synchronously control the cell cycle, DNA repair, cell aptosis, angiogenesis and regeneration in the integumentary system. The present disclosure provides a relatively broad understanding of numerous critical events detailing the control of circadian and ultradian clocks over these important processes. This will allow the development of successful "patient-tailored" photo-chrono-modulated delivery of specific and targeted light energies into different therapeutic situations.

The nature of the circadian time 24-hour cycle in the entire body and on a cellular level allows for critical prediction of important rhythmic hormonal and cell cycle biochemical peaks and troughs in human beings. These 24-hour hormonal and cell cycles events highlight important temporal occurrences such as the rest phase, growth phases and mitotic phases of the cell cycle and cellular energetics, along with cellular motility highs and lows, enzyme production and mitosis.

Various forms of chrono-disruption can alter these predictable rhythms and either flatten them or phase shift them to unpredictable peaks and troughs in areas like chronic wounds. This can transpire with such anomalous occurrances as excess or restrained systemic melatonin, glucocorticoids or other endogenous or exogenous agents. Photo-chrono-therapeutics can be easily tailored to deal with these issues on a person-to-person and case-to-case basis.

Currently, available photo-therapies treating wounds and dermal tissues does not take chronobiology into account. Therefore it is imperative to develop new strategies and devices to treat these areas from a chrono-biological perspective. Therefore there exists a need for novel methods and systems that can offer photo-chrono-therapeutics.

The following detailed description will subsequently explain non-limiting exemplary embodiments of the inventions disclosed herein.

Chronic Wounds:

When chronic wounds fail to progress through the customary events in the healing process, they then enter a state of pathologic inflammation. Integumentary cells that are present in chronic wounds have been shown to undergo phenotypic changes (changes in genetic expression) that weaken their ability to properly proliferate, migrate and respond to various growth factors and cellular signals. Furthermore, cells at the non-healing edges of human chronic wounds exhibit dysregulated expression of protein receptors for things like epidermal growth factor. However, skin cell cultures derived from normal cells (beyond the wound edge) do not exhibit chronic wound pathology Following an injury of the skin, a cascade of events occurs, which mediates the steps of tissue repair that normally concludes in the reestablishment of the epithelial layer. Wound healing and tissue repair is divided into (1) the inflammatory phase, (2) the granulation phase (i.e. the synthesis of new connective tissue) and (3) epithelial wound closure.

During the repair process there is precise interaction between various cell types that provide coordination of discrete events, allowing for a temporal and Spatial control. Approximately 12 hours after wounding, fibroblasts begin to migrate into the area from tissue proximal to the wound. 12-20 hours later, inflammation begins to recede, and forty-eight to seventy-two hours into wound healing, the cellular interactions become dominated by the interaction of keratinocytes and fibroblasts, as the wound microenvironment continues to progress away from an inflammatory to a synthesis-driven granulation stage of tissue rebuilding.

As fibroblasts migrate into the wound area, they will start the process of replacing the new blood clot with nascent collagen matrix. Fibroblast movement has been shown to be directed by the orientation of the extracellular and collagen matrix, in a phenomenon known as 'contact guidance. The extracellular matrix also affects the speed of the fibroblast migration and the composition of the ECM alters the production of different proteins by the migrating fibroblasts. A healthy extracellular matrix contains an excess of growth factors and cytokines which will also alter fibroblast behavior. Finally, fibroblasts will organize thin collagen fibrils to give support to the fibrous structure in the dermis.

The migrating fibroblasts use the collagen matrix as a scaffolding to crawl along. Thus, not only do migrating fibroblasts affect the three dimensional orientation of the extracellular matrix, but the matrix orientation also influences the directed movement of the fibroblasts. Fibroblasts are also attracted to fibronectin as it leaks from damaged capillaries and is secreted by invading leukocytes.

Hence, fibroblast migration and proliferation play extremely vital roles in the early stages of the temporo-spatial overlap of wound healing events. One major reason is because of the formation of extracellular matrix and granulation tissue in the wound via the fibroblasts.

The completion of a healed wound is always the restoration of a new intact epidermal barrier. It is recognized that a wound that is not epithelialized has not passed the threshold to be considered "healed" even if the underlying dermal structures are restored. Therefore, the re-epithelialization of a wound is the critical and defining feature of a repaired wound.

Re-epithelialization of a wound is the result the precise spatio-temporal convergence of three specific keratinocyte functions. These are (1) migration, (2) proliferation, and (3) differentiation. The spatio-temporal sequence of events by which keratinocytes complete re-epithelialization is believed to begin with dissolution of cell-to-cell and cell-to-substratum contacts, that is then followed by migration of basal and certain supra-basilar keratinocytes, over the provisional wound matrix. With this occurrence, a subset of keratinocytes immediately adjacent to the wound (but not within the wound bed) will then undergo mitosis. In conclusion, there is multi-layering of the newly formed cells (epidermis) and induction of differentiation. The most limiting part of this cycle is keratinocyte migration, as chrono-dysregulation in this step is a very frequent occurrence in chronic wounds, but not in proliferation.

In human chronic wounds, the keratinocytes at the non-healing edge of the wound are found to multiply at far higher rate than usual (hyperproliferation). It is a well-established paradigm that epithelialization is compromised in chronic wounds. In these areas, the keratinocytes around the edge of the non-healing wound are hyperproliferative and very mitotically active in the supra-basal (above the stratum basale) layers of the skin. This abhorrent occurrence produces a much thicker cornified layer around the wound (hyperkeratosis) where cell nuclei are still present (parakeratosis). Normally as keratinocytes move upward from the stratum basale, they lose their nuclei, forming sturdy layers of crosslinked proteins and creating a protective layer over the wound. However the skin cells of chronic wounds remain enucleated, unable to progress to this stage of differentiation. Thus the keratinocytes of the chronic wound seem to be trapped in the middle of these two normal processes without completing either of them.

Histopathologically, research has found that there are two fundamentally different types of tissues in proximity to each other in these wounds. The first are hyperkeratotic and hyperproliferative keratinocytes at the edge of the wound that are unresponsive to growth factors. The second are keratinocytes (adjacent to the wound in non-ulcerated areas) that are responsive to growth factor stimuli, and are healing competent. These are the findings that support aggressive debridement, to remove the thickened, hyperkeratotic, healing-incompetent (callus) cells from the area. These keratinocytes that are hyperproliferating and forming thick non-responsive wound edges, are not senescent, but are dysregulated, and therefore need to be removed. Similar histopathologic and molecular changes have been observed in most types of chronic wounds. In summary, Keratinocytes on a chronic wound edge are capable of proliferating, but are unable to migrate properly.

Finally, specifically inhibiting proper cell motility in healing incompetent keratinocytes is the presence of nuclear protein β-catenin, that inhibits migration and wound healing through the induction of expression of its downstream target gene c-myc. The expression of c-myc leads to a blockade of the epidermal growth factor RGF response and represses the expression of important cytoskeletal components that support keratinocyte migration. All current data points to the fact that healing incompetent keratinocytes at the wound edge are trapped in a vicious cycle in which preserves proliferation, allowing differentiation processes to take place in unorganized chrono-disrupted fashion, without adequate spatio-temporal control.

Cell migration (keratinocytes and fibroblasts) is obligatory for wound repair and can be divided (itself) into multi-step cyclic processes. The basic migratory cycle includes extension of a pseudopod, formation of stable attachments near the leading edge of the pseudopod, translocation of the cell forward, and finally release of adhesions and retraction at the cell rear.

Given the very complicated and precise spatio-temporal organization that is necessary for the two primary cell types to function properly in wound healing (fibroblasts and keratinocytes), the importance of irradiating these cells at the correct time in their 24-hour cell cycles becomes even more apparent. In this case, it is reasonable to apply Occam's Razor to the plethora of measurement processes that researchers have attempted to use to generate data in the past, because they have en masse performed photo-therapy without taking circadian and ultradian oscillations into account.

When applying Occam's Razor, this applicant concludes that what researchers and physicians are actually seeing in their attempts to improve wound healing with photo-therapy (without circadian and ultradian protocols) is an equal amount of chrono-disruption in these cells, as it is improvement of their functions. So as "Occam's Razor" or the "Principle of Parsimony" is often used for techniques that choose the simplest explanation as the best, the lack of any a priori knowledge of where in the cell cycle these cells are before therapy is commenced, adds indefinable amounts of variability to any data that is actually derived and reported. To alleviate this, the present inventor has formulated a method of enhanced parsimony, by using circadian and ultradian knowledge of the cells, and the cell cycle as a guide to any infrared irradiation of cellular assays and/or a patient's photo-chrono-therapy.

Figure 3:
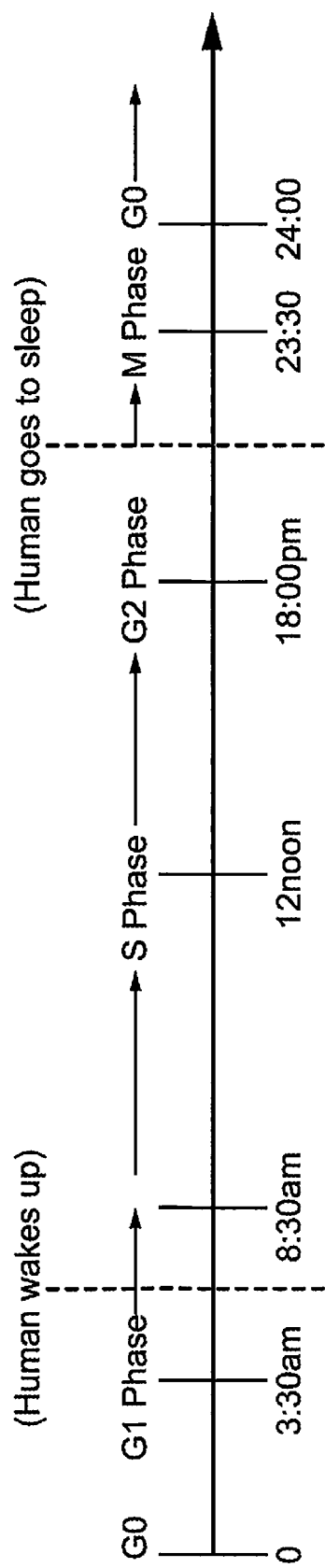
FIG. 3 is an illustration of the human circadian cycle with corresponding phases of cell mitosis.

Still further logic concerning human fibroblasts and keratinocytes may be added to the present techniques from the following data and explanations.
Circadian Periodicity in Human Fibroblasts and Keratinocytes:

It has been proven that human fibroblasts and keratinocytes have 24-hour clocks, where the stage a cell is at in the cell cycle can be predicted a priori in a patient, or in an assay, by the time of day or night, or temporal synchronization of an assay. Testing human fibroblast and kertatinocyte cells from a variety of individuals, Brown et al (2005) found that both cell types showed distinct circadian periodicity. Sandu et al (2012) also confirmed the presence of functional circadian oscillators in human primary fibroblasts and keratinocytes. Of highest import, the human cell cycle has been successfully mapped within a 24-hour period (e.g., as shown in FIG. 3), to allow predictable a priori information to be utilized (based on the time of day) concerning when vital cell cycle events occur (Levi et al 2010, Sancar et al 2010 and Gachon et al 2010)

In some embodiments, this temporal cell cycle information is vital to the present techniques. When this data is added to previous facts that in general, cell migration and motility have been found to be enhanced during G1 and early S-phase of a 24 hour cycle, compared to late S-phase and G2 (Ratner et al. 1988; Iwasaki et al. 1995; Walmod et al. 2004) its greater importance becomes clear.

Still further information concerning human eukaryotic cell migration may be added to the present disclosure from the following data and explanations.
Eukaryotic Cell Migration from the Circadian Perspective:

One of the objects of the present disclosure is to provide a technique with which to enhance the ability of fibroblasts and keratinocytes to migrate towards a selected "optical signal" at a selected time. To accomplish this, the cells first must be able to detect such a signal, then determine the direction of the signal, and finally couple this information to the endogenous apparatus that drives cellular directional movement.

Eukaryotic cells move via the use of lamellipods and filopods. These protrusions locally propel the edge of the cell outwards. If a cell is to migrate, a precise sequence of events must occur that will lead to a directional pseudopod growth, that is itself well organized in space and time. This pseudopod can also be counterbalanced by the retraction of other pseudopods from other areas on the cell surface. One of the best known ways that pseudopods are guided in their extension, is via specific chemoattractants.

The ways in which eukaryotic cells detect extracellular signals such as chemoattractants and growth factors are generally accepted and fairly well understood.

Chemoattractants will bind to transmembrane receptors on the outside of the cell, and the intracellular domains of these protein receptors will then activate specific intracellular messengers, (O-proteins), which in turn then activate other pathways. Another object of the present disclosure is to provide a means with which to have selected infrared wavelengths of light be absorbed in cell membranes and transmembrane lipo-proteins to produce nano-newton or pico-newton forces within proximity of the transmembrane receptors for pseudopod extension, so that through optically mediated mechanotransduction (e.g., as described in Bornstein, U.S. Pat. Pub. 2012/0116484 A1, published May 10, 2012), the infrared light will serve a similar process as the chemoattractant. The event is known as phototaxis and would accomplish much the same effect as chemo-attractants.

Cellular mechanotransduction essentially describes the conversion of minor mechanical forces into biochemical signals (Wang et al 2008 and 2009). Studies have shown that fibroblasts and keratinocytes will respond to an assortment of physical stimuli including (1) compression, (2) stretch, and (3) shear forces. Virtually all features of cellular behavior can be mechanically modulated in culture, suggesting that the correct optical projection and absorption in a cells membrane would produce sufficient nano-newton or pico-newton forces within proximity of the transmembrane receptors.

Keratinocytes have also been shown to be mechanically responsive (Knies et al 2006, Reichelt 2007,). Another object of the current disclosure is to accomplish optically mediated mechanotransduction and migration (Takei et al 2009) or (phototaxis) on these cells. There have actually been five major overlapping cellular pathways that have been described that can translate mechanical forces into biologic and biochemical signals. These are integrin-matrix interactions, cytoskeletal strain responses, stretch ion channels, cell traction forces (CTFs) and G protein-coupled receptors.

Therefore, without wishing to be bound by any theory and not intending to limit any aspect of the disclosure by any theory as to the underlying mechanisms responsible for the phenomena of optically mediated mechanotransduction producing infrared spatio-temporal photo-taxis, it is postulated that the wavelengths irradiated according to the present methods and systems at the specific times in the circadian cycle are absorbed by the long chain hydrocarbons in the cell membranes and lipoproteins, creating sufficient nano-newton and or pico-newton forces that would act in a similar manner to chemoattractants for directed pseudopod and lamellopod formation. This infrared spatio-temporal photo-taxis would increase the level of directed lamellopod and pseudopod creation in the direction of the infrared irradiation essentially upregulating and/or forward modulating directed lamellopod and pseudopod construction in fibroblasts and keratinocytes. This would entail irradiating a target site at the internal periphery of a wound on an individual's skin with optical radiation having wavelengths in the range of 865 nm to 875 nm and/or 925 nm to 935 nm at a dosimetry from about 0.015 W/cm^2 to 1.0 W/cm^2.

In other words, embodiments of the disclosed invention optically affects molecules that mediate cellular mechanotransduction including, but not limited to, the lipid bilayer of the plasma membrane, lipo-proteins, the extra cellular membrane (ECM), transmembrane "integrin receptors", and cytoskeletal structures.

Even if this modulation occurs by a small amount, the resulting physical force on the membrane could significantly alter cellular function and to a greater extent tissue mechanics. This is accomplished at the proper circadian time in the cell cycle, without generating substantial heat effects, and is a significant improvement over the background art, that does not a priori take into account where in the cell cycle a cell may be during irradiation.

In contrast to the prior art, other optical energies given at the wrong time are not only less than optimal for absorption by long chain hydrocarbons (cell membranes) and adipose cells but may also act as chrono-disruptors instead of mechano-transduction mediators, to cellular events, and cell cycle progression.

The present method selectively targets these unique hydrocarbon (lipid) chains of the bilayer and lipo-proteins of the plasma membranes of fibroblasts and keratinocytes, and may alter the static orientational order of the membrane lipid bilayer, with directly absorbed energy (e.g., with power on the order of milli-Watts), to optically force changes in the membrane, causing dynamic interactions of the bilayer.

This concomitant transduction then leads to conformational (structural) changes in the membrane bound proteins that catalyze and modulate pseudopod and lamellopod formation. These processes can be altered by things like physical forces on the membrane, minor changes in the extracellular matrix (ECM) that the eukaryotic cell resides in, and any changes in the basic cell structure. The molecular mechanism by which a cell senses and responds to external mechanical stress has been referred to as "cellular mechanotransduction".

The molecules that mediate cellular mechanotransduction include the lipid bilayer of the plasma membrane, the ECM, transmembrane "integrin receptors", and cytoskeletal structures. Therefore, any external stimulus or device that may cause optical interference with the normal cell membrane thermodynamics (without generating substantial heat effects) and hence cause cellular mechanotransduction to the plasma membrane and biochemical pathways at the proper spatio-temporal time in the cell cycle for the maximum desired effect, is an advantageous improvement over prior known laser therapies.

Hence, if the lipid bilayer actively absorbs optical energy in milli-watt doses, at about 870 and/or about 930 nm, for example, causing increased kinetic interactions on a molecular level in the molecular bonds that make up the membrane (but in the absence of a significant temperature increase) the membrane will appreciate free energy addition and mild mechanotransduction forces that could significantly alter cellular function and to a greater extent the integumentary tissue being irradiated.

Minute mechanical forces can regulate a cells biochemical activity in a manner that is equally as potent as chemical or pharmacological signals. This means that slight deformations in a cell membrane or lipoprotein (because of the increased kinetic energy associated in the lipid bilayer of the cell membranes with about 870 nm and/or about 930 nm optical absorption) can and will cause remarkable conformational changes to the vital trans-membrane proteins. This could be a direct ramification of cellular mechanotransduction via the increased kinetic energy of the C—C and C—H bonds in the lipid bilayer from 930 nm optical energy absorption.

Collectively, these mechanotransduction pathways demonstrate how both biochemical and structural mechanisms can modulate the response to minor forces. A highly complex signaling network is available to the cell that allows cells to dynamically engage with their physical environment like optically mediated mechanotransduction producing infrared spatio-temporal photo-taxis. One intracellular pathway that would potentially be of principal importance in embodiments of the current invention for infrared spatio-temporal photo-taxis would be the signalling lipid phosphatidyl inositol 3,4,5-trisphosphate (PtdIns(3,4,5)P3), as it is strongly involved in cell migration.

Infrared spatio-temporal photo-taxis signals would potentially bias normal fibroblast and keratinocyte movement by altering the rate of pseudopod growth or biasing the position at which new pseudopods are generated. Another mechanism for the phenomenon would be an optically mediated mechanotransduction interaction with signalling pathways and pseudopods that would re-direct signalling bias in the pseudopod movement machinery. Where the "noise" and confusing signals from other sources, generated by chronic inflammation in a chronic wound could generate significant randomness in biochemical mobility pathways, embodiments of the present invention could act as a "lighthouse in a storm" to accurately present directional information to translocating cells, towards the interior of a wound.

Eukaryotic Cell Mechanosensation from the Circadian Perspective:

The majority of the known cellular mechano-sensors are understood to act by changing the conformational state of proximal protein or ion channels in response to an applied external force. In various tests of the membrane lipid bilayer, a variety of compression tests have shown that the cell membrane under normal physiological conditions is essentially "volumetrically incompressible", so that different mechanical perturbations actually result in a localized thinning of the membrane. This thinning of the membrane causes a parallel conformational change in associated proteins proximal to the mechanical perturbation, as the mechano-sensors in cell membranes actually "sense minor newton forces".

It is also known that cells can sense force through coupling, via transmembrane proteins such as integrins, between the extracellular matrix and the cytoskeleton. When under stress, the cytoskeleton will undergo a rearrangement of its actin and intermediate filaments and microtubules, tripping different biochemical cascades in the cell. Cellular mechanosensing may also be mediated by a force driven conformational change in cytoskeletal proteins, that can affect protein function.

Another example of potential optical mechanosensing, leading to optically mediated mechanotransduction, that produces infrared spatio-temporal photo-taxis is irradiation about 870 nm and/or about 930 nm in proximity of the membrane of a fibroblast or keratinocyte, that will be transmitted to the cytoskeleton of the cells. In mammalian cells, the cellular organelles, nuclei and most importantly the cell membrane lipid bilayer are interrelated and organized by a comprehensive series of cytoskeletal filaments. Many of these are also connected and linked with ECM molecules by means of specific receptors on the outside of the cell membrane that as transmembrane receptors are still connected to the cytoskeleton. The biochemical regulation of a cell's shape, function and motility is mechanically controlled by the structural and functional geometry of these intra- and extra-cellular systems in the cytoskeleton of cells including keratinocytes and fibroblasts.

The mammalian cytoskeleton is a highly integrated network of fibers, filaments and polymers all formed within the cell as part of normal function. Any mechanical modification of this network of cytoskeletal fibers (such as increase of kinetic energy from absorption of the wavelength about 870 nm and/or about 930 nm optical energy in keratinocyte or fibroblast membrane) can alter the chemical environment of the cell, and potentially induce changes in cell shape, motility and metabolism, by changing the molecular dynamics of the cell.

The cytoskeleton is actively implicated in a range of cell functions that include force transduction and production, cell membrane modulation, hormone secretion, intracellular transport, organelle translocation, and cell migration. The cytoskeleton serves to provide a measure of mechanical stiffness to resist cell deformation in the face of forces like fluid flow dynamics, or mechanical stresses from surrounding tissues. Even though it is still being actively researched to completely explain how the physical mechano-transduction and concomitant deformation of a cell membrane protein or cytoskeletal component can lead to a given biochemical response, it has been suggested in many tissues that this network of filaments, once deformed, will change the membrane tension force in cells and alter things like mechanosensitive ion and nutrient channels and enzymes.

The molecules that mediate cellular mechano-transduction include the lipid bilayer of the plasma membrane, the ECM, transmembrane "integrin receptors", and cytoskeletal structures. Therefore, any optical external stimulus or device that may induce optically mediated mechanotransduction and further produce infrared spatio-temporal photo-taxis will beneficially alter the normal cell thermodynamics at the membrane level, and potentially cause directed pseudopod and lamellopod formation through up-regulate cellular enzymatic motility processes.

There has also recently been a new model described by Gov et al (2003, 2004, 2005) and Lin et at (2006) which analyzes cellular mechanical vibrations based on the membrane-bound cytoskeleton. These mechanical vibrations can probably drive important oscillations of electrically polar transmembrane proteins, and generate further electric oscillations. In this model, the frequency range of the oscillations is 12/minute to 1800/minute as described by Krol et al. (1990).

Lamellopodia and Pseudopodia from Endogenous Membrane Waves

Cell migration through the formation of Lamellopodia is generally separated into a series of overlapping steps: (Sheetz 1999)

1) Membrane, protrusion from actin polymerization (growth) and polymerization force.
2) Adhesion of the protrusion at the protrusion front.
3) An actin—myosin-powered contraction of the cytoplasm,
4) A release of cellular adhesions at the rear of the cell
5) Finally, a forward translocation of the cell body and recycling of the motility machinery.

There have been many reports (Brosteanu et al 1995) of "actin traveling waves" (actin t-waves) that travel around the perimeter of human keratinocytes in specific spatiotemporal behaviors and progressions. To promote these t-waves, the actin system appears to "self-organize" into waves that propagate on the membrane of a cell. It has also been shown in fibroblasts, that the local oscillations of protrusions and retractions at the edge of the membrane are linked to the waves of actin, myosin light chain kinase and alpha-actinin, both of which (Giannone et al 2004 and 2007) travel in a rearward and lateral direction along the cell, some of them measured every 24 seconds.

Unlike "objects", waves (wave motion) do not exhibit any repulsion of each other when they come in contact. The physics of waves allow two patterns to overlap in the same region of space. When two waves coincide, they add together. A simple example would be that in a certain location (for example two actin t-waves on a fibroblast or keratinocyte membrane) at a certain moment in time, each wave would have a crest 2 microns above the normal plane of the membrane. The waves would combine to make a 4 micron crest in the membrane. This would possibly be a trigger for the growth of a pseudopod. If one were measuring troughs, negative numbers would be used to make a 4 micron trough. A 2 micron crest and a 2 micron trough would momentarily cancel each other out to become flat with the plane of the membrane. This simple additive rule of waves in this instance would be classified as actin t-wave "superposition". This actin t-wave superposition can occur not just with sinusoidal waves, but with waves of any shape, or with wave pulses (short duration waves).

Figure 5A:
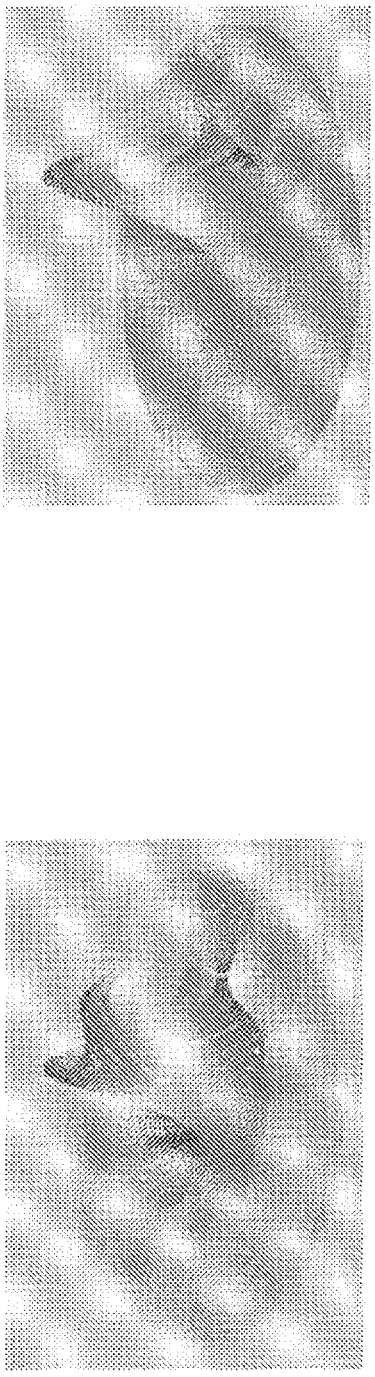
FIGS. 5A and 5B are an illustrations of a technique for optically directed formation of a pseudopod in a cell membrane.
Figure 5A:
Figure 5B:
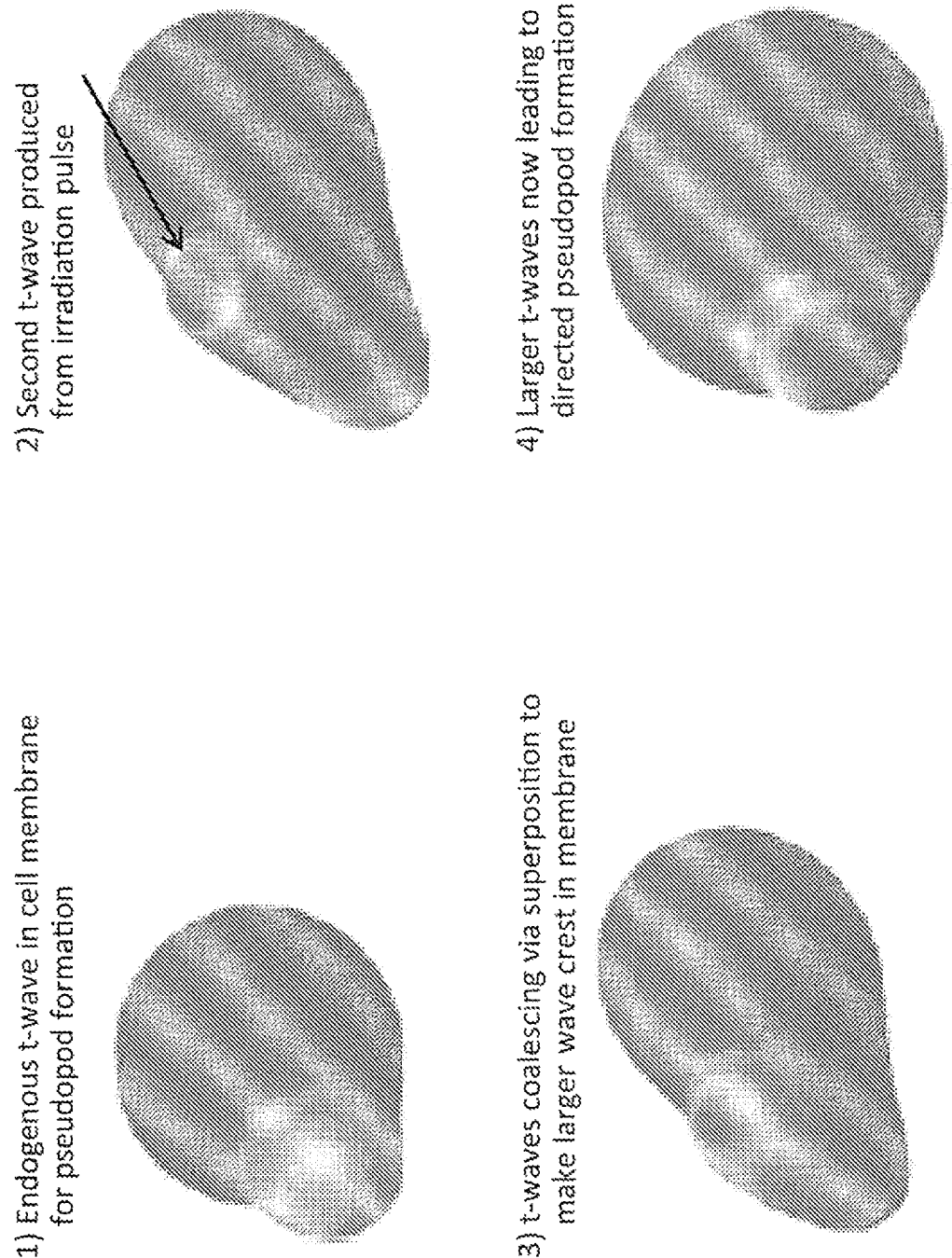

For example, FIGS. 5A and 5B illustrate the enhancement of an endogeonous actin t-wave in a fibroblast or keratinocyte membrane. In pane 1, an endogenous t-wave has formed in the cell membrane. In pane 2, a second t-wave is introduced in the membrane by applying a pulse of near-infrared irradiation (in close proximity to the cell) synched to the ultradian periodicity of the formation of the endogenous wave, e.g., using any of the techniques described herein. In pane 3, the externally created wave and the endogenous wave coalesce to produce an enhance wave. As shown in pane, 4, the enhanced wave will then lead to directed pseudopod formation. Accordingly by applying the irradiation with a selected directionality (e.g., as described herein by selectively irradiating a portion of a wound inward from the wound margin), cell migration can be biased towards a desired direction.

Recent observations oft-waves in keratocytes also demonstrate sequential waves, in which the subsequent wave appears shortly after the previous wave extinguishes. It has also been suggested that to induce t-waves, one could use local oscillations as pacemakers. A time series analysis video has also recorded in keratinocytes lamellipodial protrusions at the cell periphery that have definite periodicity, of approximately 150 seconds, with a wave front of approximately 10-20 microns wide. Similarly, in a recent paper studying the migratory cells Dictyostelium discoideum, Driscoll et al (2012) came to the conclusion that wave-like protrusions provide a simple and robust mechanism for directed migration.[3]

Finally, reports vary in different cell lines as to the timing and periodicity of waves and migration appendages. As an example, fibroblasts (generally) exhibit a relatively slow and uncoordinated movement with protruding and retracting lamellipodia. Fibroblasts also contain numerous stress fibers connected to large focal adhesions. It is now commonly accepted, that actin waves and the regulation of actin dynamics is associated with lamellopodia and pseudopodia, cell-matrix adhesion, and cell migration.

Wound Management:

Chronic wound management, e.g., for Diabetic patients, takes many different forms. Properly preparing the wound bed can remove many unambiguous obstructions to healing. These obstructions include but are not limited to: (1) necrotic tissue, (2) wound exudate, (3) bacteria and fungus, (4), many types of abnormal cells.

It is widely believed that diabetic ulcers and wounds will heal more quickly with sharp and forceful repeated debridement of these obstructions, although evidence is scant. Necrotic material can also be removed from the wound bed with different debriding agents such as (a) enzymes, (b) hydrogels, and (c) hydrocolloids, although evidence for their efficacy is also limited. Various antiseptics have also been tried such as silver and iodine, but again clear evidence for their use is limited.

There has also been attention focused on controlling leg and foot edema, which has shown some benefit (with a foot compression device) after sharp and forceful repeated debridement. Recently, there has been substantial interest in the therapeutic potential of adding exogenous growth factors on the wound to stimulate fibroblast and keratinocyte migration into the center of the wound. This event (fibroblast and keratinocyte migration) aids in the deposition of extracellular matrix, collagen formation and the eventual re-epithelization of the wound.

The generally recognized steps in wound healing are the following three overlapping phases: (1) Inflammation, (2) Granulation tissue formation and re-epithelialization (3) Wound contraction, extracellular matrix deposition and remodeling.

The techniques described herein may be used to determine favorable time(s) for chrono-photo-therapy, when in the biology of a wound, the inflammation is decreasing, and the granulation stage is commencing, that then leads to enhanced proliferation of fibroblast and keratinocyte cell translation towards the interior of the wound. In some embodiments, an infrared light source may be used that can specifically deliver a dose of 870 nm, 870 nm/930 nm and or 930 nm energy to a wound site just inside of the wound margins, and outside of the wound margins, as the fibroblasts and keratinocytes migrate towards the interior of the wound from the non-healing margins.

As discussed above, with proper debridement, (i.e. the removal of hyperkeratotic, infected, and nonviable tissue from a wound) a new environment can be established in a non-healing wound that places "normal phenotype" fibroblasts and keratinocytes directly adjacent to the non-healing edge of the wound. This will then increase the chances for optically mediated mechanotransduction, that produces infrared spatio-temporal photo-taxis., and more normal autocrine and paracrine secretion of growth factors such as endogenous leptin from the hypodermis. This will give these cells a better ability to migrate towards the center of the wound.

The following example described herein analyzes the time-dependent cell cycle events in terms of eukaryotic cell motility from numerous research data points. Favorable time(s) for chrono-photo-therapy may be determined. The ensuing data progression is applied logically with a thought experiment, that will distill the information through the "prism" of chrono-photo-biology to conclude that, in various embodiments, an improvement may be realized, and optimization of therapy may occur, based on selected infrared treatment at specified times in the cell cycle.

(a) It has been observed that mouse 3T3 fibroblasts would extend their pseudopodia towards distant near infra-red sources, e.g. latex particles which scattered light. Albrecht-Buehler (1991)[37]

(b) There is evidence that cells have changing and different mechanical properties at different stages of interphase in the cell cycle. For example, the viscosity of the cytoplasm has been shown to increase nearly 1.5-fold from the G1 to S-phase of the cell cycle. (Tsai et al. 1996).

(c) There is an observed increase in adhesion force of cells to their extracellular environment as cells progress from the G1 phase to the S phase, and then to the G2/M-phase. This increase in adhesion force coincides with a gradual reduction in cellular migration speeds (Giet et al. 2002).

(d) A study of cultured hematopoietic stem cells revealed lowest migration being observed in the G2/M phase. (Giet et al. 2002).

(e) Cell migration and motility have been found to be enhanced during G1 and early S-phase of a 24 hour cycle, compared to late S-phase and G2 (Ratner et al. 1988; Iwasaki et al. 1995; Walmod et al. 2004).

This information may be used as a basis for specifying time of infrared irradiation to enhance photo-biologic effects of optically mediated mechanotransduction, that produces infrared spatio-temporal photo-taxis.

Initially, the evidence for point (a) above is reviewed. Albrecht-Buehler (1991) reported a series of experiments in which he manipulated mouse 3T3 Fibroblasts to investigate the effect of infra-red light on the cells various functions and properties. He observed that mouse 3T3 fibroblasts would extend their pseudopodia towards distant near infra-red sources, e.g. latex particles which scattered light. Albrecht-Buehler found that when he exposed the base of the cell tail (opposite side of the leading edge of a lamellopod) to attempt to reverse the cells from translating forward, that a large percentage would actually extend a lamellopod towards the light in the rear, ostensibly reversing their direction. The light exposure lasted for between 1-3 hours, with a power density of 1.5 mW/cm^2 and sinusoidally oscillating amplitude at a frequency of 30 pulses/minute. The peak wavelength that this occurred at was approximately 900 nm. Albrecht-Buehler reported that the cells were able to reverse their polarity and move toward the infrared spot.

Albrecht-Buehler then conducted a second set of assays, to test the ability of the mouse fibroblasts to extend new lamellipodium towards distant sources of scattered infrared light 10-100 microns away from the cells. Here again, they found that the 3T3 cells were able to aim new surface projections directly at the scattered light sources. They irradiated the "scatter particles" with different wavelengths, and found the strongest response to these experiments at around 800 nm and 900 nm at a power density of 1.5 mW/cm^2 with a sinusoidally oscillating amplitude at a frequency of 60 pulses/minute. At the time, Albrecht-Buehler (1991) postulated that perhaps a cellular "vision" aids the cells in locating a chemical gradient (chemotaxis) by detecting altered infrared emissions in the direction of the source. Albrecht-Buehler had previously postulated that "a cells cytoplasm has a certain capacity of data processing and integration."

However, Albrecht-Buehler failed to apply this finding to provide therapeutic treatments of the types disclosed herein. Consider a non-healing chronic wound that has been recently debrided. The area of this hypothetical wound is 2 cm^2 and the attempts at different forms of therapy (for example; wound vac, laser, VEGF gel etc) have all taken place diurnally the day from 9:00 am to 5:00 pm. Referring to FIG. 3, showing the correspondence of mitotic cell phases to the 24 hour day for a typical patient, this "daytime" treatment protocol, which is normal and customary in the present art of wound healing, would fall squarely in the fibroblast and keratinocyte time frame of the S-phase, G2-phase, and early Mitotic phase of the cell cycle, which is exactly the circadian time of "least motility" for these cells. Because of the inhibited motility, the area of this hypothetical wound is not closing despite multiple attempts to alleviate the chronic nature of the epidermal and dermal deficiency.

One may construct an infrared optical system that will take into account the patients circadian rhythm, based on data inputs for example, (a) time patient went to sleep, (b) time patient woke up, (c) time of highest endogenous cortisol level (e.g., measured daily over 7-10 days). Such a system with wavelengths of about 870 nm and about 930 nm that would be calibrated to treat the patient at the proper time for maximal motility of fibroblasts and keratinocytes (G1 phase to early S-phase) in the cell cycle would be extremely beneficial. This would be between approximately 1:00 am and 6:00 am for most patients, when they were sleeping.

This system may be configured with annular solid or pinpoint beam projections (e.g., of the type shown in FIG. 4), that would irradiate inside the wound, proximal to the newly debrided healing edge, so that the fibroblasts and keratinocytes would undergo optically mediated mechanotransduction, that produces infrared spatio-temporal phototaxis, and cause directed translocation of these vital cells to the interior of the wound. This system can measure the patient's ultradian cardiac rhythm and modulate the applied treatment light based on that rhythm, e.g., to establish an intensity pulsed treatment with between 30 and 90 pulses/minute.

Figure 4:
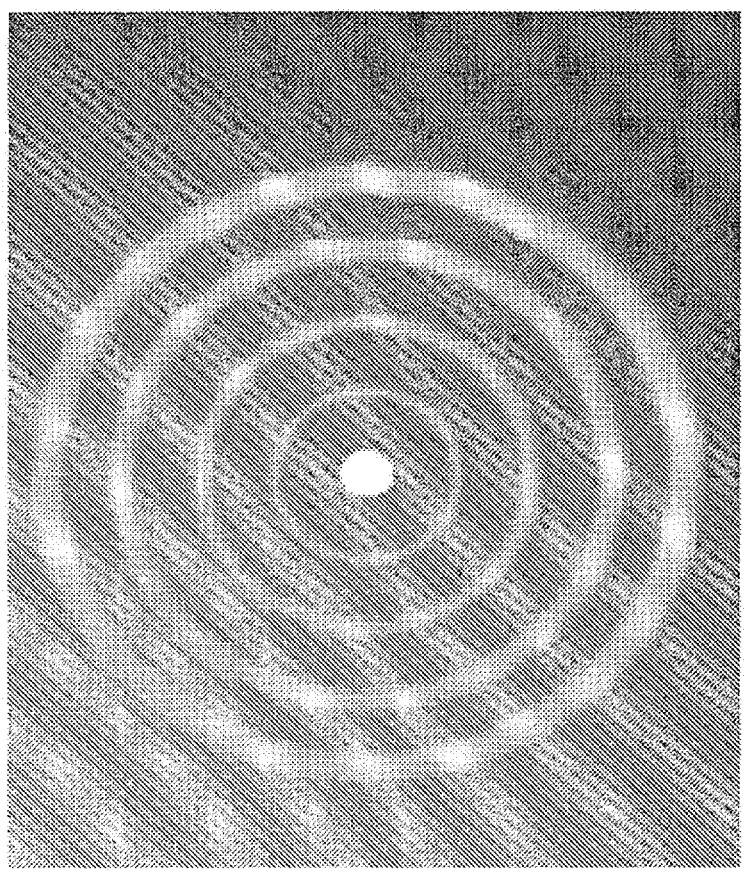
FIG. 4 is an illustration of illumination patterns for a photo-crono-therapy system.

As many chronic diabetic wounds suffer from a lack of the spatially decentralized contraction-relaxation cycle of the heart that is transmitted to the cell membranes because of diabetic vascular disease, hence, re-establishing that patients specific ultradian oscillations within the wound, via the light pulses synchronized to the patient's heart rate may be accomplished by the above described technique. This personalized optical re-establishment of the patients own ultradian oscillation would improve or optimize (for each patient) the mechanotransductive environment necessary to enhance the migration potential of the fibroblasts and keratinocytes from the wound margins. These cells would locate and respond to the pulsed near infrared optical energy (e.g., 870 nm, 870 nm/930 nm and/or 930 nm energy), and migrate towards it in the direction of the interior of the wound. The diameter of this energy delivery to the wound site would be controlled to progressively get smaller, in multiple therapies, as the wound diameter contracted and continued to heal (e.g., as shown in FIG. 4).

Circadian and Local Leptin Production and Wound Healing.

Plasma leptin is secreted in a circadian pattern from adipocytes in the human body, with superimposed ultradian pulses in healthy individuals Sinha et al 1996 and Licino et al 1997). The highest level of adipose leptin secretion in humans has been measured at between 2:00 am and 6:00 am in the morning (Ahmad et al 2001).

Leptin is also actively produced in the wound environment throughout the inflammatory and proliferative stages of integumentary tissue repair. Leptin up-regulation begins immediately after the infliction of a wound. It has been shown that even though leptin is expressed constitutively in adipose tissue, after wounding adipocytes increase their level of leptin production. In regard to the wound environment, leptin is a known pro-angiogenic factor that is probably an active contributor to the neovascularization process that accompanies wound healing. Two examples of this would be that leptin increases re-epithelialization and accelerates wound healing (Frank et al 2000), and impaired wound closure and contraction has been observed in excisional wounds that were treated with leptin neutralizing antibodies. Therefore, it can be reliably stated that normal wound healing requires acute local production of leptin and a working leptin signaling system at the wound site (Murad et al 2003). Finally, leptin has also been proven to be produced from not only fibroblasts and keratinocytes, but also subcutaneous adipose tissue, via correct stimulation (Tomonobu et al 2007, Glasoe et al 2001, Peura et al 2011).

In various embodiments, one may determine favorable time(s) for chrono-photo-therapy, when on the outside of the wound edge leptin production can be augmented by optically mediated mechanotransduction (e.g., as described in Bornstein, U.S. Pat. Pub. 2012/0116484 A1, published May 10, 2012). This technique may include increasing leptin production in hypodermis around a wound, without generating significant heat in, or significant damage to the adipocyte in the hypodermis. This would entail irradiating a target site at the external periphery of a wound on an individual's skin above subcutaneous adipose tissue with optical radiation having wavelengths in the range of 925 nm to 935 nm at a dosimetry from about 0.015 W/cm^2 to 1.0 W/cm^2. In some embodiments, one may directing the optical radiation to the target site, e.g., with a uniform intensity "top hat" in an area corresponding to an annulus around the outer margin of the wound. In some embodiments, the difference between the inner and outer radius of this annulus may be at least 1 mm, at least 1.5 mm, at least 2 mm or more.

The following prophetic example analyzes the time-dependent circadian events in terms of human leptin production to determine favorable time(s) for chrono-photo-therapy administration for wounds. An available experimental data progression is applied logically with a thought experiment, that will distill the information through the "prism" of chrono-photo-biology to conclude that an improvement will be realized, and optimization of therapy will occur, based on selected infrared treatment at specified times in the circadian leptin secretion cycle and the cell cycle of fibroblasts and keratinocytes.

The following example is based on the following observations know to be true in a typical subject:
(a) The highest level of adipose leptin secretion in humans has been measured at between 2:00 am and 6:00 am in the morning.
(b) Leptin is also actively produced in the wound environment throughout the inflammatory and proliferative stages of integumentary tissue repair.
(c) Leptin up-regulation begins immediately after the infliction of a wound and it has been shown that even though leptin is expressed constitutively in adipose tissue, after wounding adipocytes increase their level of leptin production.

The above data may be used to extrapolate a basis for specifying time of infrared irradiation to enhance photobiologic effects of optically mediated mechanotransduction for enhanced leptin production (e.g., using the techniques described in Bornstein, U.S. Pat. Pub. 2012/0116484 A1, published May 10, 2012) in the annulus around the periphery of a wound.

Consider a wound that has been recently debrided. The area of this hypothetical wound is 3 cm^2 and the attempts at different forms of therapy (for example; wound vac, laser, VEGF gel etc) have all taken place diurnally the day from 9:00 am to 5:00 pm. This "daytime" treatment protocol, which is normal and customary in the present art of wound healing, would fall squarely in the time frame of troughs in the circadian production of leptin secretion from human adipose tissue. This would also be the late cell cycle phase of the resident fibroblast and keratinocyte cells that would be in the S-phase, G2-phase, and early Mitotic phase of proliferation (i.e. decreased motility). Because of the circadian leptin trough and the late stages of the cell cycle, the area of this hypothetical wound is not closing despite multiple attempts to alleviate the chronic nature of the epidermal and dermal deficiency during the daytime "light" hours of normal Doctor/Patient therapy.

One may construct an infrared optical system that will take into account the patients circadian rhythm, based on data example inputs including, e.g., 7-10 days of (a) time patient went to sleep, (b) time patient woke up, (c) time of highest endogenous leptin level. Such a system with wavelengths of about 870 nm and about 930 nm that would be calibrated to treat the patient at the proper time to coincide with maximal endogenous leptin production, to increase and/or augment the leptin production in the periphery of the wound. This would be extremely beneficial to the healing of the wound, and would occur between 1:00 am and 6:00 am for most patients, when they were sleeping.

This system may be configured with annular solid or pinpoint beam projections, that would irradiate outside of the wound (either alone or simultaneously with irradiation to enhance cellular phototaxis inside the wound) proximal to the newly debrided healing edge, so that increased leptin production would occur in subcutaneous adipose tissue for maximal autocrine and paracrine effect on the wound. This system can be connected to the patients ultradian cardiac rhythm, to establish, e.g., between 30 and 90 pulses/minute. The diameter of this energy delivery to the outside perimeter of the wound site would progressively get smaller, in multiple therapies, as the wound diameter contracted and continued to heal.

Another prophetic example analyzes the time-dependent circadian events and temporal periodicity in terms of the human inflammatory response. Incorporating an understanding of this response will increase the probability of leading to optimized clinical treatment times for chronic wound therapies. An available experimental data progression is considered in view of the chrono-photo-biological techniques described herein to conclude that an improvement will be realized, and optimization of therapy will occur, based on selected infrared treatment at specified times in the circadian inflammatory response cycle and the cell cycle of fibroblasts and keratinocytes.

The following example is based on the following observations know to be true in a typical subject:
(a) Circadian rhythms are important parameters in the human inflammatory response because several significant components of the immune system have noteworthy circadian patterns.
(b) Inflammatory cytokines experience circadian variations in blood plasma concentrations, and characteristically reach a peak at night.
(c) Plasma glucocorticoids (cortisol) concentrations will also display a circadian pattern, where they peak in the early morning.
(d) Due to the immune-modulatory effects of glucocorticoids with their robust circadian pattern in the plasma, cortisol is believed to be involved in the circadian entrainment of cytokine production from leukocytes.
(e) It has been shown that cortisol (in the morning) (i) stimulates the production of anti-inflammatory cytokines, and (ii) inhibits the production of pro-inflammatory cytokines.
(f) A second probable circadian regulator, melatonin, peaks at night, while falling to low resting levels in the morning and for the balance of the day. Melatonin has been shown to stimulate the production of cytokines.

As chronic wounds are "chronically inflamed" understanding the temporal periodicity of the inflammatory response is very important as the potential for an inflammatory response is greatest at night, and is significantly lower during the late morning and daytime.

When cortisol levels are high, during the day, the human system is protected from a heightened inflammatory response. But when cortisol levels are low, natural variations in cytokine levels result in periods of time when the human system is primed for a heightened inflammatory response.

The conclusion is that numerous studies have provided strong links between circadian rhythms and the immune system. Simple changes in therapeutic practices that take into account the time of day may affect chrono-photobiology outcomes to the positive.

Consider a wound that has been recently debrided. The area of this wound may be, e.g., 1.5 cm^2 and the attempts at different forms of therapy (for example; wound vac, laser, VEGF gel etc) may have all taken place diurnally the day from 9:00 am to 5:00 pm. This "daytime" treatment protocol, which is normal and customary in the present art of wound healing, would fall squarely in the time frame of high cortisol, that stimulates the production of anti-inflammatory cytokines, and inhibits the production of pro-inflammatory cytokines. This would also be the late cell cycle phase of the resident fibroblast and keratinocyte cells that would be in the S-phase, G2-phase, and early Mitotic phase of proliferation (i.e. decreased motility). Any therapy at this time could possibly act as a chrono-disruptor, instead of an enhancer of therapy. Because of the S-phase, G2-phase, early Mitotic proliferation of the fibroblasts and keratinocytes in the wound, the area of this hypothetical wound would not close adequately during the daytime "light" hours of normal Doctor/Patient therapy, with chrono-disruption.

One may construct a an infrared optical system that will take into account the patients circadian rhythm, based on data example inputs including, e.g., 7-10 days of (a) time patient went to sleep, (b) time patient woke up, (c) time of highest G0 post-mitotic and non-proliferative or quiescent phase of the cell cycle. Such a system that would treat the wound at the cellular quiescent phase (at night), generating spatio-temporal photo-taxis through causing optically mediated mechanotransduction, even in the face of inflammatory chrono-disruption from circadian elevated cytokines, would be a clear improvement over current therapy.

Such a system with wavelengths of about 870 nm and about 930 nm that would be calibrated to treat the patient at the proper time to now coincide with maximal inflammatory cytokine production, that normally inhibits cellular locomotion in the periphery of the wound. Thus, chrono-phototherapy would potentially cause incompetent cells at the wound edge (trapped in a vicious cycle in which preserves proliferation, allowing differentiation processes to take place in unorganized chrono-disrupted fashion, without adequate spatio-temporal control) to now undergo directed cellular locomotion, which would be extremely beneficial to the healing of the wound, and would occur between 1:00 am and 6:00 am for most patients, when they were sleeping.

This system may be configured with annular solid or pinpoint beam projections, that would irradiate outside of the wound (either alone or simultaneously with irradiation to enhance cellular phototaxis inside the wound) proximal to the newly debrided healing edge, so that increased leptin production would occur in subcutaneous adipose tissue for maximal autocrine and paracrine effect on the wound. This system may be connected to the patient's ultradian cardiac rhythm, e.g., to establish between 30 and 90 pulses/minute. The diameter of this energy delivery to the outside perimeter of the wound site would progressively get smaller, in multiple therapies, as the wound diameter contracted and continued to heal.

Intentional Wounding of Photo-Damaged and Wrinkled Skin

Examined clinically, photoaged skin is wrinkled, leathery and blotchy. From the histological perspective, there are dyskeratotic (abnormal keratinization occurring prematurely within individual cells or groups of cells below the stratum corneum) keratinocytes with distinct evidence of epidermal atrophy. There are currently a variety of ways to induce a clinical "wound" in a photodamaged area, in an attempt to stimulate a superior result with newly healed integumentary tissues. Some examples of these purposeful and induced wounding modalities are:

a) A chemical peel. This is a technique employed to improve and smooth the texture of skin by means of a chemical solution that causes "dead skin" to slough off and eventually peel off. The regenerated skin is usually smoother and less wrinkled than the old skin.

b) Dermabrasion. This is a surgical procedure of "skin planning" that employs a (wearing away) of the upper to mid layers of the skin with strong abrasive devices. The procedure typically removes the top to deeper layers of the epidermis, and extends into the reticular dermis, where there is always minor skin bleeding. Depending of the level of skin removal with dermabrasion, it takes an average of 7-30 days for the skin to fully heal (re-epithelialize). Dermabrasion has largely been replaced other newer technologies such as lasers.

c) Photorejuvenation. This is a skin treatment that employs very strong and fast light pulses (such as intense pulsed light) to treat a variety of skin pathologies and wrinkles. The process induces controlled wounds on the skin, thereby prompting it to heal itself by creating new cells.

d) Laser resurfacing. This is a skin treatment employing a high power laser, considered true surgery, where it is used to treat a variety of skin pathology such as sun damage, scars, wrinkles stretch marks and spider veins. Laser resurfacing is generally performed today at 2940 nm Er:YAG laser, or a 10,600 nm CO2 laser. A more modern technique is now performed with a fractional laser system of differing wavelengths. The fractional laser employs a series of miniature pinpoint beams to deliver the laser energy to the surface of the skin in only a fraction of the area. There can be hundreds or thousands of pinpoint beams used per square inch of skin, leaving healthy skin in between the ablated tissue areas. This allows more rapid healing to occur.

As discussed above, with proper inducement of a clinical wound, a stimulated healing and superior result with newly healed integumentary tissues can be effected that will cause the result of regenerated skin that is smoother and less wrinkled than the old skin. The systems and/or methods used herein are to determine favorable time(s) for chrono-phototherapy, when used on induced wounds of any type, performed to attempt to improve photodamaged and wrinkled skin. This method would comprise optically mediated mechanotransduction to increase leptin production around the induced wound and infrared spatio-temporal photo-taxis of keratinocytes and fibroblasts in the induced wound. The dual effect would be enhancing autocrine and paracrine secretion of endogenous leptin from the hypodermis, and up-regulating recruitment of fibroblasts and keratinocytes into the induced wound. This will give these cells a enhanced ability to migrate towards the center of the wound, causing the wound to heal faster, with superior results, such as enhanced thickness and smoothness of contour.

This would entail irradiating a target site at the external periphery of the induced wound on an individual's skin above subcutaneous adipose tissue with optical radiation having wavelengths in the range of 925 nm to 935 nm at a dosimetry from about 0.015 W/cm$^2$ to 1.0 W/cm$^2$; and directing the optical radiation to the target site with a top hat distribution.

One may construct an infrared optical system that will take into account the patients circadian rhythm, based on data inputs including 7-10 days of (a) time patient went to sleep, (b) time patient woke up, (c) time of highest endogenous leptin level. Such a system with wavelengths of about 870 nm and about 930 nm that would be calibrated to treat the patient at the proper time to coincide with maximal endogenous leptin production, to increase and/or augment the leptin production in the periphery of the induced wound. This would be extremely beneficial to the healing of the wound, and would occur between 1:00 am and 6:00 am for most patients, when they were sleeping.

This system may be configured with annular solid or pinpoint beam projections, that would irradiate inside wound (either alone or simultaneously with irradiation to enhance optically mediated mechanotransduction of enhanced leptin production) proximal to the edge of the induced wound, so that it would be calibrated to treat the patient at the proper time for maximal motility of fibroblasts and keratinocytes (G1 phase to early S-phase) in the cell cycle. This would be between 1:00 am and 6:00 am for most patients, when they were sleeping. This would entail irradiating a target site at the internal periphery of the induced wound area(s) on an individual's skin above the induced wound with optical radiation having wavelengths in the range of 865 to 875 and/or 925 nm to 935 nm at a dosimetry from about 0.015 W/cm^2 to 1.0 W/cm^2; and directing the optical radiation to the target site with a top hat distribution. This would cause the wound to heal faster, and potentially recruit more cells than would otherwise be recruited in the normal healing process, to improve the thickness and strength of the newly healed skin. These occurrences of improved skin thickness, smoothness of contour, and strength, as a result of embodiments of the present invention would be novel extended benefits, to any wounding therapy and technology used to address wrinkled or photo-damaged skin.

Optically Mediated Mechanotransduction and Collagen Synthesis

The most plentiful proteins in the extracellular matrix are different members of the collagen family. The collagens are the extracellular scaffolding and the major structural element of all connective tissues and the extracellular matrix. They contribute to the stability of tissues and allow organs to maintain their structural integrity. Collagen is a term for the proteins that form the distinctive triple helix of three polypeptide chains, and all members of the collagen family form supra-molecular structures in the ECM although their different sizes and tissue function and distribution may differ significantly. Even with large structural diversity among the many different categories of collagen types, all members of the collagen family have the unique characteristic of a right triple helix composed of three alpha-chains.

In the cytoplasm, mRNA is translated into pre-pro collagen, which protrudes into the lumen of the rough endoplasmaic reticulum. After processing and procollagen assembly, the triple-helical molecules are then packaged within the Golgi bodies of cells, and retained into secretory vesicles that are released into the extracellular space.

Following this secretion, procollagen trimers are then processed in different manners, depending on the collagen type. Collagen that is produced in fibroblasts is made as a larger precursor procollagen. As the procollagen is secreted from the cell, it is acted upon by specialized enzymes called procollagen proteinases that remove extension peptides from the ends of the molecule thereby processing it into true collagen. The second stage occurs in the extracellular space, with another post-translational modification, where the triple helical collagen molecules form fibrils and then fibers. The third stage is a reaction that places stable crosslinks within (intra-molecular crosslinks) and between the molecules (inter-molecular crosslinks) in the growing collagen chains. This is the critical step that gives the collagen fibers such tremendous strength.

There is evidence that mid-infrared radiation of fibroblasts has effects on wound healing through greater collagen regeneration and infiltration of the fibroblasts into a wound. In Toyokawa H, et al., 2004, they performed a far infrared study on Rat Wounds, and 2004, Hutson et al., described the peak of mid-infrared absorption for human collagen to be 6.45 microns. This peak absorption is as a result of an amide-ii absorption group in collagen, that at 6.45 microns has 6× higher absorption than water.

As discussed above, with a peak absorption in the mid infrared for collagen, the systems and/or methods used herein are to determine favorable time(s) for chrono-phototherapy, when used on wounds of any type, comprised of a light source from 6.35 microns to 6.55 microns to perform optically mediated mechanotransduction to increase collagen synthesis in fibroblasts. This can be accomplished by greatly increasing the amount of collagen and the tensile strength and character of healing wounds. This effect would be used to (with or without other wavelengths in embodiments of the present invention) to manipulate the fibroblast proteome.

This would entail irradiating a target site inside an induced or non-induced wound, where fibroblasts had already migrated, at a dosimetry from about 0.015 W/cm^2 to 1.0 W/cm^2; and directing the optical radiation to the target site with a top hat distribution. One may construct a 6.45 micron optical system that will take into account the patients circadian rhythm, that would be calibrated to treat the patient at the proper time to coincide with the greatest potential to synthesize collagen, that would occur between about 1:00 am and 6:00 am for most patients, in the G1 or s-phase of the cell cycle. This system may be configured to cause the wound to heal faster, and potentially make the new skin stronger, and improve the thickness and smoothness of the newly healed skin.

Figure 9B:
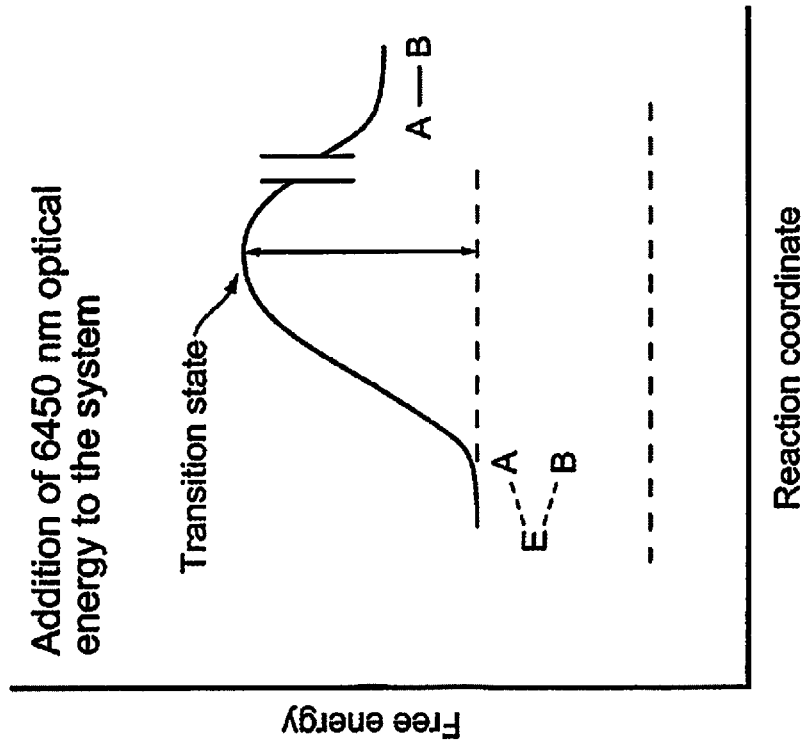
FIGS. 9A and 9B illustrate the reduction of activation energy barrier for collagen formation in the presence of 6.45 micron infrared light.
Figure 9A:
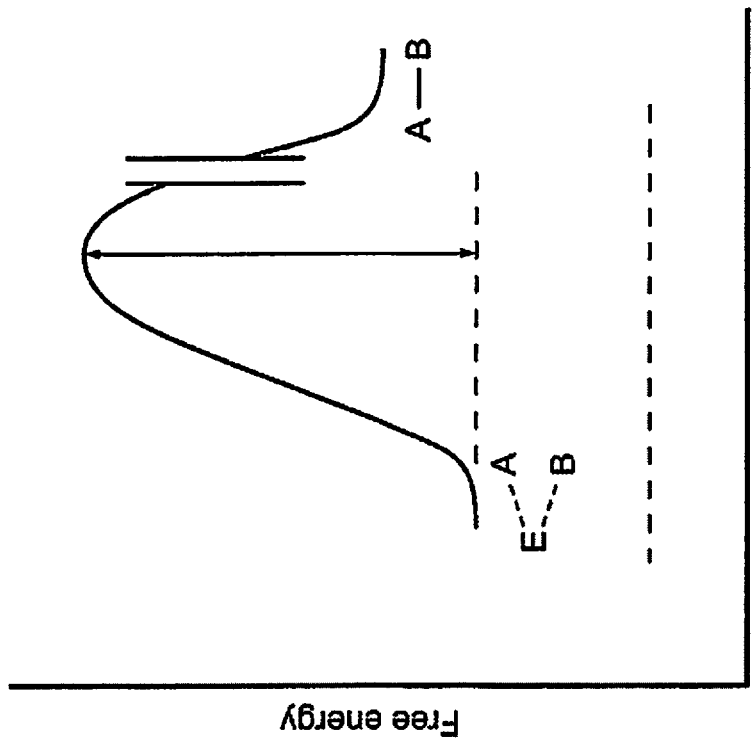

FIGS. 9A and 9B illustrate how the addition of this (6.45 micron) optical energy at defined dosimetries would enhance collagen synthesis by adding small amounts of vibrational energy to the (pro-collagen and collagen) proteins thereby assisting collagen molecule positioning in the active sites of the necessary enzymes in the collagen synthesis cascade (inside and outside of the cell). This would produce a lower activation energy for these collagen synthesis enzymes when reacting with the collagen proteins. This would allow an up-regulation of collagen synthesis as the collagen proteins become more accessible to the active sites. Hence, the formation of an enzyme mediated transition state would happen more frequently, by lowering the transition state barrier, thus decreasing the activation energy of the reaction, and causing it to occur faster.

Some embodiments include providing accelerated wound healing by use of a mid infrared light source, to emit infrared energy at a wavelength at 6.45 microns to further enable these processes.

In various embodiments, mid-infrared light, e.g. at a wavelength of 6.45 microns, may be applied to a subject (e.g., at a wound site) with a suitable dosimetry to promote regenerative healing. In some embodiments, the laser light may be applied with a power density at the treatment sight in the range of 0.01-0.49 W/cm^2, or any subrange thereof. The laser light may be applied for any suitable treatment time, e.g., in the range of 1 minute to 2 hours or any subrange thereof. In some embodiments, the laser light may be applied with an energy density at the treatment sight in the range of 0.5-3500 J/cm^2, or any subrange thereof. The infrared light may be provided, e.g., using a quantum cascade laser, a lead salt laser, a laser system using difference frequency generation techniques, etc.

Figure 1B:
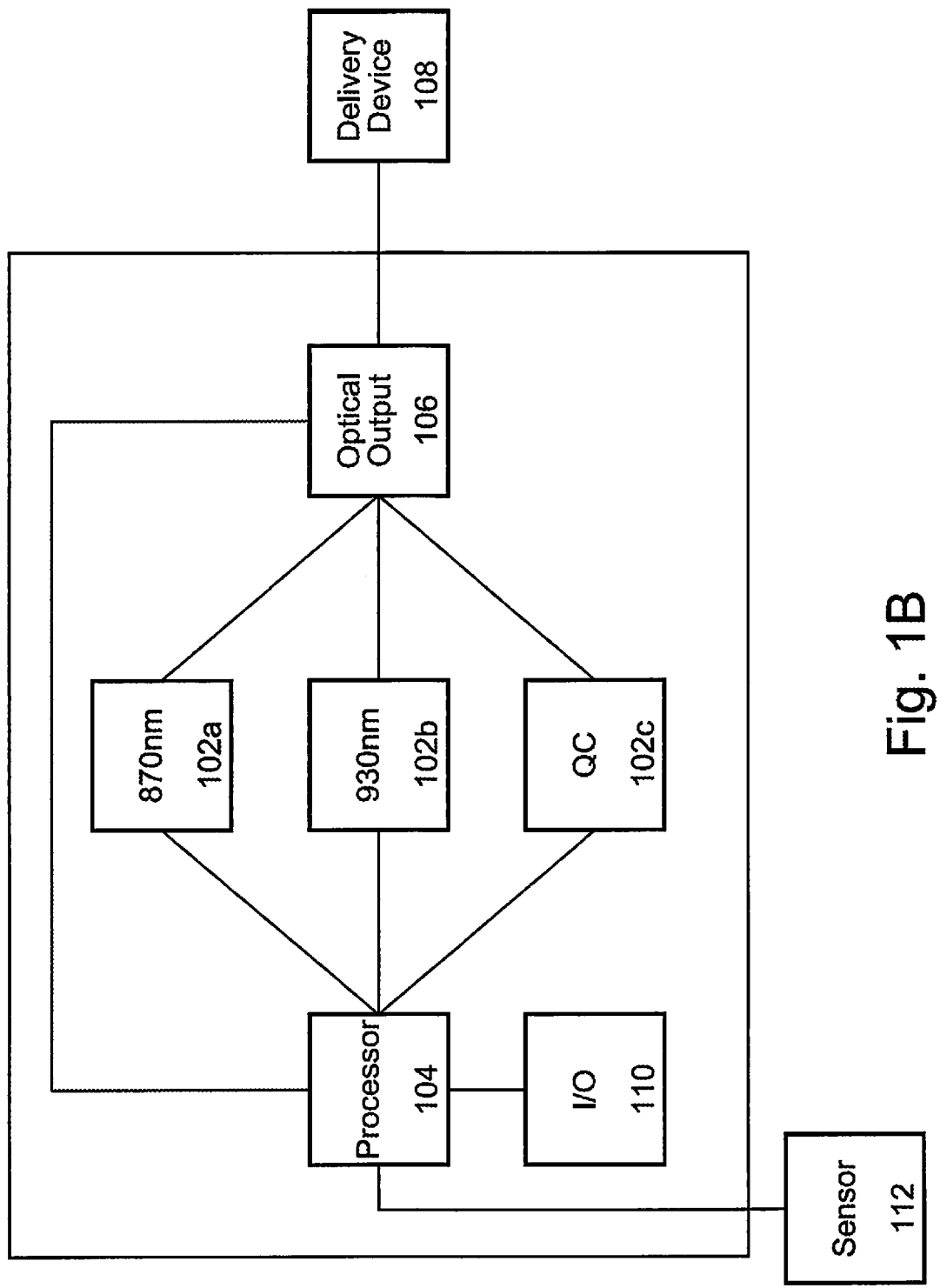
FIG. 1B is a block diagram of the system of FIG. 1A.

In some embodiments, the mid-infrared laser may be integrated into a single system which also provides treatment light at near-infrared wavelengths described herein (e.g., as shown in FIGS. 1A and 1B).

Exemplary Photo-Chrono-Therapeutic System and Method

FIGS. 1A and 1B illustrate a system 100 for providing photo-chrono-therapeutic treatment to a subject. As shown, the system 100 is used to promote healing of a wound on the arm of a human patient 101, however it is to be understood that in various embodiments, system 100 may be used to implement any of the various treatment techniques described herein.

The system 100 includes one or more sources of therapeutic treatment light 102 (as shown, three sources 102a, 102b and 102c) controlled by a processor 104. Light from the sources 102 is received by an optical output device 106 and directed to a delivery device 108. The delivery device 108 applies the treatment light to the patient 101. In some embodiments, the processor 104 may also control the operation of the optical output device 106 and the delivery device 108.

The system 100 may also include an input/output (I/O) module 110 operatively coupled to the processor 104 to facilitate user control or and monitoring of the system 100. As shown, the I/O, module 110 includes a display screen (e.g., a touch sensitive screen) and four control buttons, but it is to be understood that in various embodiments any other type of control or display may be used.

In some embodiments, each of the light sources 102 may provide therapeutic treatment light in a desired range of wavelengths. For example, as shown, the sources 102a and 102b are near infrared light sources having different output wavelength ranges, and the source 102c is a mid-infrared light source.

In some embodiments, the light source 102a generates optical radiation substantially in a first wavelength range including wavelengths at or near the wavelength 870 nm (e.g., from about 850 nm to about 900 nm, or any subrange thereof such as from about 865 nm to about 875 nm, or from about 869 nm to about 871 nm).

The light source 102b generates optical radiation substantially in a second wavelength range including wavelengths at or near the wavelength 930 nm (e.g., from about 910 nm to about 950 nm, or any subrange thereof such as from about 925 nm to about 935 nm or about 929 nm to about 931 nm).

The light source 102c generates optical radiation substantially in a third wavelength range including wavelengths at or near the wavelength 6.45 microns (e.g., from about 6.35 microns to about 6.55 microns, or any subrange thereof such as from about 6.40 microns to about 6.5 microns or about 6.44 microns to about 6.46 microns).

In some embodiments, for each source, at least 80%, 90%, 95%, 99%, or more of the optical power emitted by the light source is emitted at wavelengths in the desired wavelength range.

For example, in some embodiments, sources 102a and 102b may be a light emitting diode (LED) sources or diode laser sources, while source 102c is a quantum cascade laser.

However, in various embodiments any suitable light source may be used, including, for example, laser light sources such as a solid stated laser diode, a variable ultra-short pulse laser oscillator, or an ion-doped (e.g., with a suitable rare earth element) optical fiber, a quantum cascade laser (e.g., for mid-infrared emission). Other suitable laser sources including those with other types of solid state, liquid, or gas gain (active) media may be used.

In some embodiments, non-laser light sources may be used including, for example a light emitting diode, an array of light emitting diodes, or a lamp (e.g., using one or more wavelength selective filtering elements).

The processor 104 controls the sources 102 and other elements of the system 100 to apply a desired dosimetry, e.g., suitable to implement one or more of the treatment techniques described herein. The processor may include a memory for storing a patient's profile and a dosimetry calculator for calculating the dosage needed for a particular target site based on the information input by an operator or acquired using one or more sensors. The memory may also be used to store information about different types of disorders or diseases and an associated treatment profile, for example, the pattern of the radiation and the dosage of the radiation, associated with a particular treatment.

In some embodiments, processor 104 controls the light sources 102 such that near infrared light is delivered from sources 102a and 102b with a suitable dosimetry to promote mitotic events, or any event that would be beneficial to regenerative healing. In some embodiments, the near infrared light may be applied to the patient 101 (e.g., at a wound site) with a power density at the treatment sight in the range of 0.01-1.0 W/cm$^2$, or any subrange thereof (e.g., 0.015 W/Cm$^2$-0.49 W/cm$^2$). The light may be applied for any suitable treatment time, e.g., in the range of 1 minute to 2 hours or any subrange thereof. In some embodiments, the light may be applied with an energy density at the treatment sight in the range of 0.5-3500 J/cm$^2$, or any subrange thereof. Further examples of suitable dosimetry for various treatment techniques are provided herein.

Similarly, processor 104 controls the light sources 102 such that mid-infrared light, e.g. at a wavelength of 6.45 microns, is delivered to the patient 101 (e.g., at a wound site) with a suitable dosimetry to promote regenerative healing. In some embodiments, the light may be applied with a power density at the treatment sight in the range of 0.01-1.0 W/cm$^2$, or any subrange thereof (e.g. 0.015 W/cm$^2$-0.49 W/cm$^2$). The light may be applied for any suitable treatment time, e.g., in the range of 1 minute to 2 hours or any subrange thereof. In some embodiments, the laser light may be applied with an energy density at the treatment sight in the range of 0.5-3500 J/cm$^2$, or any subrange thereof. Further examples of suitable dosimetry for various treatment techniques are provided herein. Further examples of suitable dosimetry for various treatment techniques are provided herein.

The optical output device 106 receives light output from the sources 102 and delivers the light to the delivery device 108 for application at the treatment site on the patent 101. In some embodiments, the output device 106 may include one or more optical elements (e.g., reflective, refractive, diffractive, or other elements) used to couple light from the sources 102 into an optical fiber, light guide, or similar device for transmission to the delivery device 108. In various embodiments, the output device 106 may include optical elements arranged to partially or completely overlap light from two or more of the sources such that they travel along a common beam path. In some embodiments, the light from different sources may be delivered along separate paths, e.g., using a dedicated optical fiber for each source, or for each of a selected class of sources. For example in some embodiments, light from the near infrared sources 102a and 102b may be delivered using a first optical fiber, while light from the mid-infrared source 102c is delivered using a second optical fiber.

In various embodiments, the processor 104 may control the sources 102 so that light from each source is applied serially (e.g., using any suitable time-based multiplexing scheme), simultaneously, or a combination thereof.

The processor 104 may receive information, e.g., signals from e.g., one or more sensors 112 indicative of biological state of the patient 101. Information from these signals may be processed, and used to control the delivery of treatment light from the sources 102. For example, the sensor signal may be indicative of a circadian or ultradian cycle in the patient 101, and the processor 104 may process this signal to synchronize the delivery of treatment light to this cycle.

As shown, the sensor 112 includes a pulse oximeter sensor that produces a signal indicative of the cardiac pulse of the patient 101. The processor 104 may use this signal to synchronize a pulsing of one or more of the sources 102 to the cardiac pulse, e.g., to implement photo-crono-therapeutic treatment techniques of the type described herein.

In various embodiments other suitable sensors may be used including, for example, an electrocardiogram, sphygmomanometer or other blood pressure sensor, a thermometer, an electroencephalography sensor, or any other suitable sensor. In some embodiments, multiple sensors may be used, e.g., a first sensor used to detect the circadian cycle of the patient 101 (e.g., for use in synchronizing treatment with the G1 and early S-phase of the cycle, as detailed herein), and a second sensor used to detect an ultradian cycle of the patient 101.

In some embodiments, the information about the biological state of the patient 104 may not be measured using a sensor, but instead received, e.g., from an external source or an internal memory. For example, in some embodiments, the processor 104 may determine information indicative of the circadian cycle of the patient 101, based on input information including, for example, (a) time patient went to sleep, (b) time patient woke up, (c) time of highest patient endogenous cortisol level (e.g., measured daily over 7-10 days). In some embodiments the processor 104 may simply receive information directly indicative of the circadian cycle, e.g., input by a user or retrieved from memory. For example, in some embodiments, the information may be a selected treatment time period corresponding to a desired portion of the circadian cycle for the patient 104.

The delivery device 108 operates to deliver the treatment light to the treatment site on patient 101 with a desired spatial pattern and intensity distribution. For example, as described herein, in some embodiments it may be desirable to provide light in a pattern that corresponds to the shape of the wound. For example, in cases where treatment light is used to stimulate cell migration into the wound, it may be desirable to selectively illuminate a peripheral portion of the wound site inward from an outer margin of a wound.

For example, referring to FIG. 4, the near infrared light may be applied by the delivery device 108 in an annular pattern, e.g., around the periphery of a wound to promote cell migration towards the center of the wound. In some embodiments the delivery device may allow the size of the annular patter to be selectively varied using any suitable technique (as shown, four different sized annular patters, and one spot patter are provided). In some embodiments, the illumination may be varied by adjusting one or more optical elements in the delivery device 108 (e.g., using an adjustable magnification telescope), by swapping out optical elements, or by any other suitable technique.

In some embodiments, the delivery device 108 may be configured to provide different spatial patterns and intensity distributions for light from different sources 102. For example, in some embodiments, the delivery device 108 provides a first light pattern for near infrared light from the sources 102a and 102b (e.g., a ring or annular pattern) while providing a second light pattern for mid-infrared light from the source 102c (e.g., a top-hat, trapezoidal, or Gaussian spot pattern).

In general, the delivery device may include suitable optical components to provide any desired pattern. In some embodiments, the pattern may be adjusted by the processor 104 based on information about the wound (e.g., a digital image of the wound). In various embodiments, the processor may implement, e.g., machine vision algorithms to determine the shape and position of the wound margin, and adjust the illumination pattern accordingly using, e.g., one or more processor controlled optical elements.

Figure 6B:
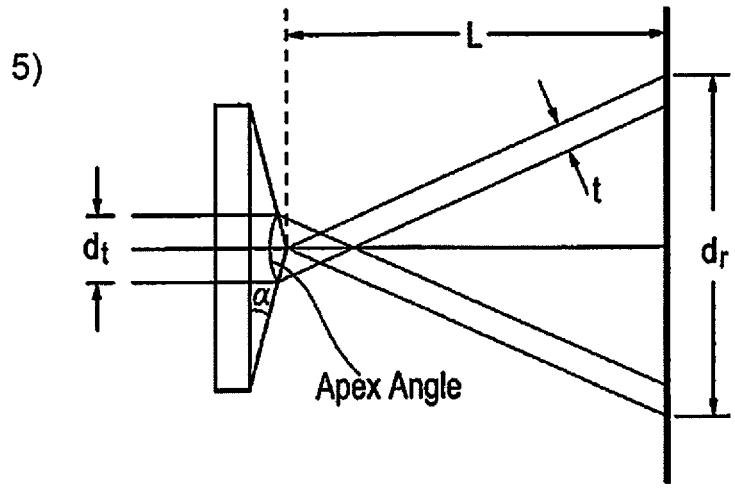
Figure 6B:
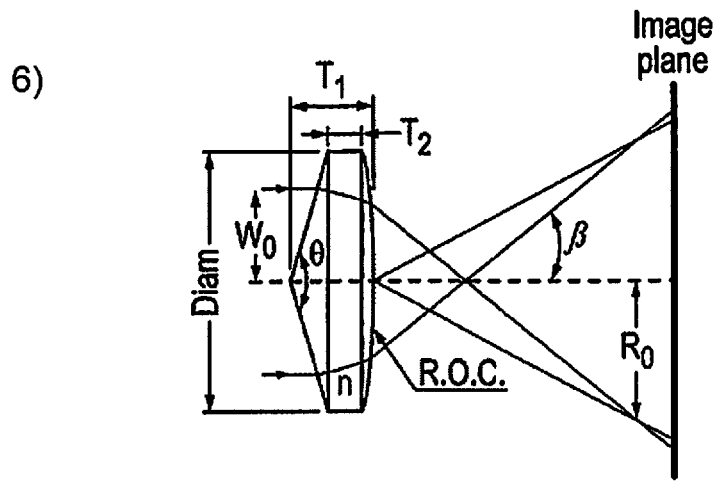

FIGS. 6A and 6B show examples (1-6) of optical elements suitable for generating annular illumination patterns. The elements in FIG. 6A include 1) an axicon convex lens, and 2) axicon concave lens, and 3) a meniscus axicon lens. Also shown is 4) a surgical rod lens suitable for generating a spot shaped illumination pattern. In addition, the elements in FIG. 6B include 5) elements of an apex angle are shown, and in 6) elements of a lense with a radius of curvature (R.O.C.) is shown.

Figure 7B:
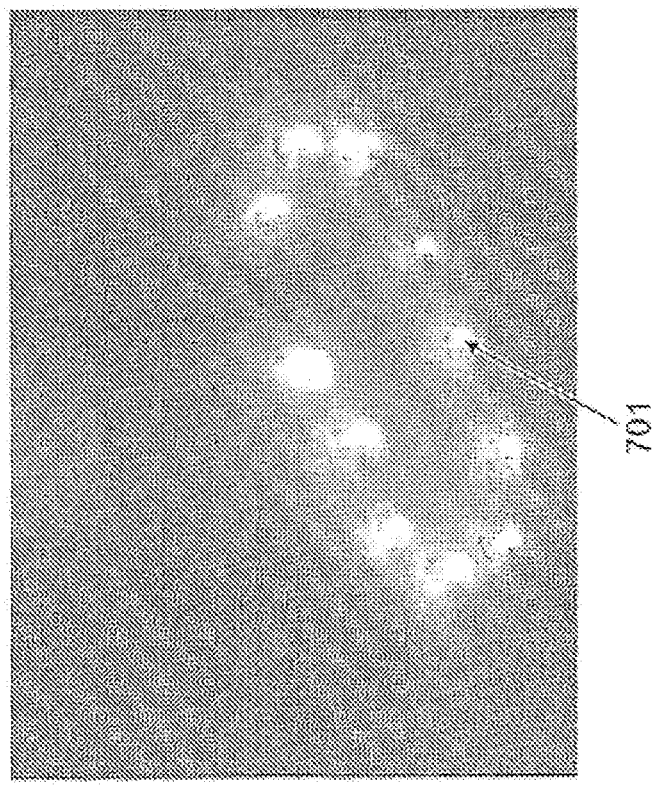
FIGS. 7A and 7B show a delivery device in a photo-crono-therapy system integrated into a sterile bandage. The FIG. 7A shows the device un-illuminated
Figure 7A:
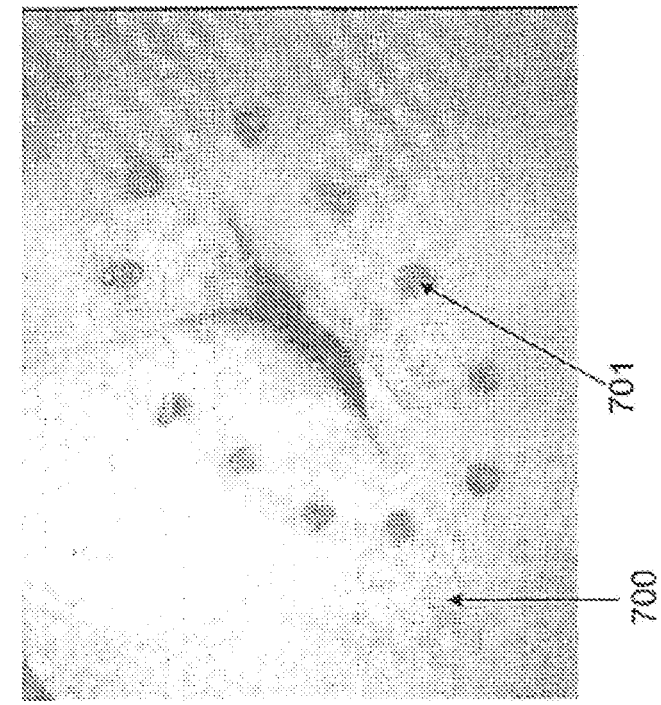
Figure 8:
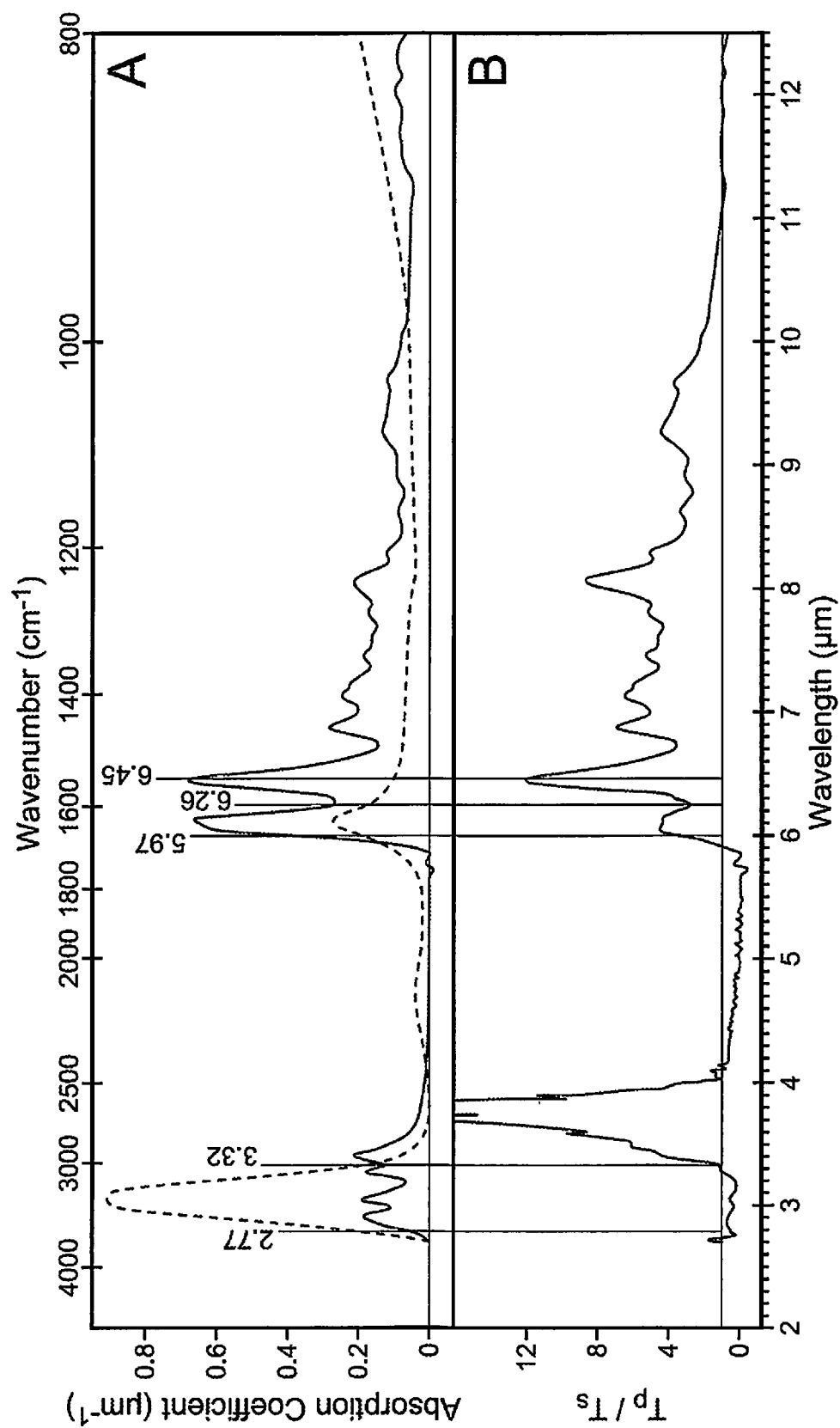
FIG. 8 shows a play of the absorption spectrum of collagen in the mid-infrared wavelength range.

In some embodiments, all or a portion of the delivery device 108 may be connected to or incorporated in structure to be applied to or worn by the patient 101. For example, the delivery device may be incorporated in a bandage or other dressing (e.g., as shown in FIGS. 7A and 7B), an article of clothing (e.g., a sleeve for an arm wound or a sock for a foot wound), or a medical support (e.g., a brace or cast). In other embodiments, the delivery device 108 may include a hand piece or the like to allow a user to direct application of the treatment light.

FIGS. 7A and 7B show an example of such a device featuring a sterile bandage 700 with a ring of embedded light sources 701. As shown, the light sources are embedded optical fibers that transmit light from one or more sources (e.g., sources 102a and 102b). The positioning of the sources may be selected to provide a desired illumination pattern. For example, as shown the ring of sources would provide a substantially annular illumination pattern at the wound.

In some embodiments, all or a portion of the delivery device 108 may be detachable or disposable. For example, in some embodiments, a set of bandages may be provided that can be attached to the system 100, each bandage in the set include a delivery device 108 configured to provide a different light delivery pattern. A suitable bandage from the set may be selected by a used to provide a suitable treatment pattern, e.g., based on a visual inspection of the size and shape of a wound at the treatment site.

In some embodiments where the delivery device 108 is a detachable or disposable unit, the unit may include one or more elements in communication with the processor 104 that may be used to confirm that the attached delivery device is compatible with the system 100. For example, each detachable unit may include an encrypted memory that can be read by the processor (e.g., through a wired or wireless communication channel) to identify the unit. If the unit is not recognized by the processor 104, the processor 104 may output an alarm condition and inhibit output of treatment light.

As shown, the system 100 is an integrated unit provided in a single housing on a standard hospital IV stand. However, it is to be understood that in various embodiments, the system may take any suitable form factor. In various embodiments, the system may include multiple components in multiple housings. For example, in some embodiments, the system 100 may include a first component used for application of near infrared light from the sources 102a and 102b, and a second component used for application of mid-infrared light from source 102c. In such a case, the components may be controlled by a common processor 104 (as shown) in FIG. 1B, or multiple processors.

Figure 2:
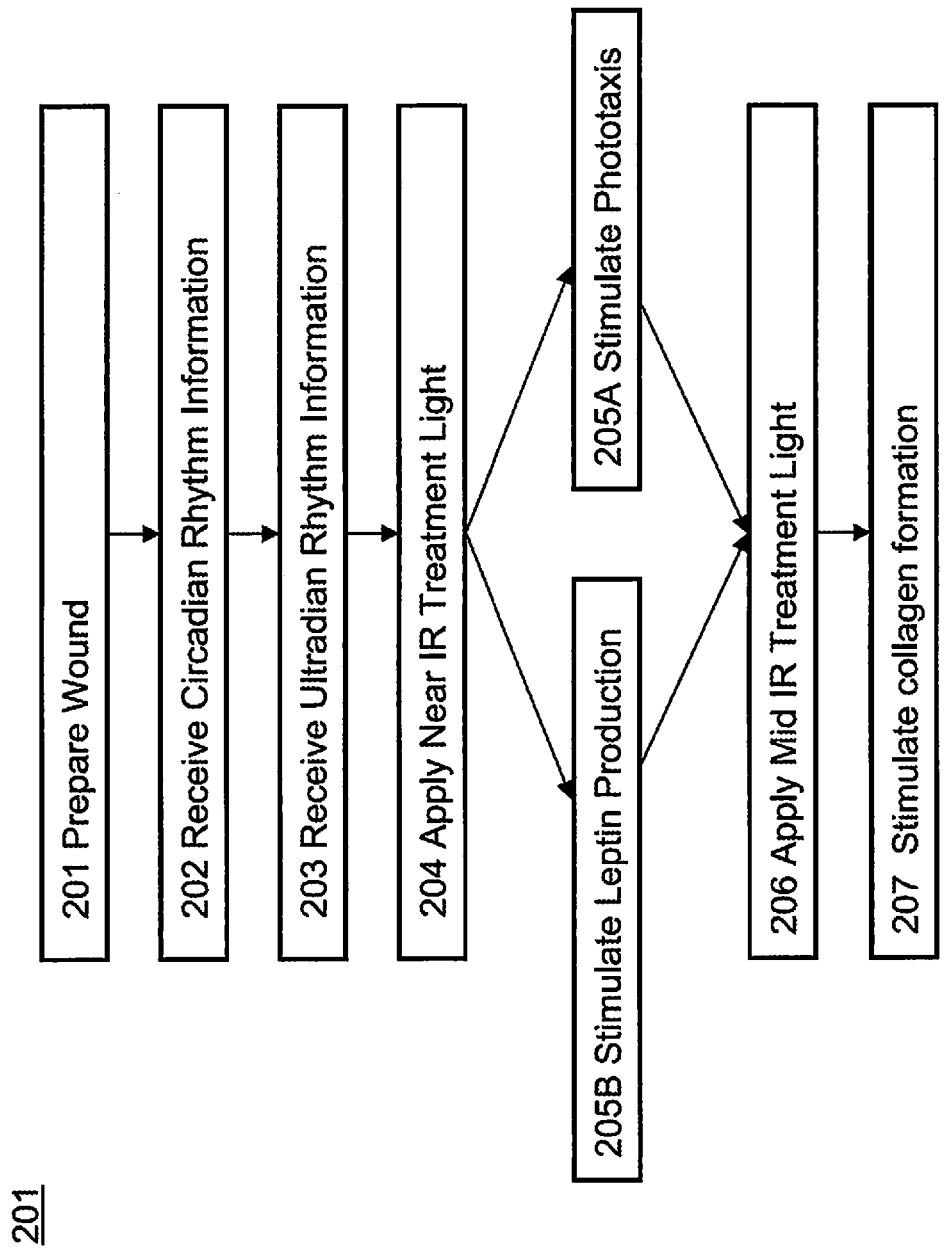
FIG. 2 is a flow diagram for a photo-crono-therapy, e.g., of the type implement by the system of FIG. 1A.

FIG. 2 shows a process flow for an exemplary method 200 of photo-chrono-therapy for promoting healing in a wound (e.g., a wound in a diabetic, or a wound caused by a cosmetic procedure) in a patient based on the techniques described herein, and suitable for implementation using the system 100.

In step 201, the wound in prepared using any suitable technique including, for example, cleaning or debrement.

Once the wound is prepared for treatment, in steps 202 and 203 information is received (or determined) indicative of the circadian and ultradian rhythms of the subject. However, it is to be understood that in some embodiments, information regarding one of the two types of rhythms may be omitted.

In step 202, the circadian rhythm information may be determined using any suitable metric, e.g., based on the patient's sleep schedule and/or endogenous cortisol levels. In step 203, the ultradian rhythm information may be determined (e.g., continuously or repetitively determined) using one or more sensors, e.g., a sensor used to determine the cardiac pulse of the patient.

In step 204, a photo-chrono-dose of near infrared light is applied to the wound site. As described herein, the treatment time (relative to the patient's circadian and/or ultradian cycles), duration, dosimetry, and special pattern may be controlled to provide a desired effect.

For example, in step 205A, the photo-chrono-dose is controlled to provide phototaxis of fibroblasts and keratinocytes from the periphery of the wound into the central portion of the wound. As detailed above, phototaxis may be stimulated by applying near-infrared light at or near 870 nm and/or 930 nm to a region at the periphery of the wound (e.g., in an annulus pattern located inside or overlapping the margin of the wound). In some embodiments, the near-infrared illumination is provided at a dosimetry from about 0.015 W/cm^2 to 1.0 W/cm^2; (e.g., a levels selected to avoid substantial thermal damage).

In some embodiments, the intensity of the applied light is modulated in time with the ultradian rhythm (e.g., the cardiac pulse) of the patient based on the information acquired during step 203. This synchronization may be particularly advantageous in diabetic patent's, were reduced vascular performance may have resulted in a loss of endogenous ultradian synchronization of cellular processes at the wound cite.

In some embodiments, the near-infrared treatment light may be applied during an advantageous phase of the patient's circadian cycle, based on the circadian information obtained in step 202. For example, in some embodiments the near-infrared light treatment may be applied at times corresponding to high photo-chrono-efficacy and/or photo-chrono-tolerance, e.g., during times corresponding to the G1 and/or early S phases of the cell cycle. In patients with typical sleep schedules, this period may correspond to the hours when the patent is asleep (e.g., 1:00 AM to 6:00 AM).

In step 205B, the photo-chrono-dose is controlled to stimulate leptin production at the wound site, e.g., in adipose cells. As detailed above, leptin prodiction may be stimulated by applying near-infrared light at or near 870 nm and/or 930 nm to wound site and/or the surrounding area.). In some embodiments, the near-infrared illumination is provided at a dosimetry from about 0.015 W/cm^2 to 1.0 W/cm^2; (e.g., a levels selected to avoid substantial thermal damage).

In some embodiments, the light may be applied in an annulus surrounding the wound. In some embodiments, the light is applied with a substantially uniform intensity distribution (e.g., a top hat distribution), to provide beneficial access to adipocytes in the hypodermis (e.g., using the techniques described in Bornstein, U.S. Pat. Pub. 2012/0116484 A1, published May 10, 2012). In some embodiments, step 205B is performed concurrently with step 205A. However, in various embodiments, steps 205A and 205B may be performed separately, serially, partially concurrently, or in any other suitable manner.

In some embodiments, the near-infrared treatment light may be applied during an advantageous phase of the patient's circadian cycle, based on the circadian information obtained in step 202. For example, in some embodiments the near-infrared light treatment may be applied at times corresponding to high endogenous leptin production. As detailed above, in patients with typical sleep schedules, this period may correspond to the hours when the patent is asleep (e.g., 2:00 AM to 7:00 AM).

In step 206, mid infrared light a photo-chrono-dose of near infrared light is applied to the wound site. As described herein, the treatment time (relative to the patient's circadian and/or ultradian cycles), duration, dosimetry, and special pattern may be controlled to provide a desired effect.

In step 207, the photo-chrono-dose is controlled to stimulate collagen generation at the wound site. As detailed above, collagen generation may be stimulated by applying near-infrared light at or near 6.45 microns to wound site and/or the surrounding area. In particular, the mid-infrared light may be directed to regions that have previously experience in-migration of fibroblasts and/or keratinocytes. In some embodiments, the mid-infrared light is used to irradiate a target site inside wound, where cells had already migrated. In some embodiments, the mid-infrared illumination is provided at a dosimetry from about 0.015 W/cm^2 to 1.0 W/cm^2; (e.g., at levels selected to avoid substantial thermal damage). I some embodiments, the illumination is provided to the target site with a top hat distribution.

In some embodiments, the mid-infrared treatment light may be applied during an advantageous phase of the patient's circadian cycle, based on the circadian information obtained in step 202. For example, in some embodiments the mid-infrared light treatment may be applied at times corresponding to G1 and/or early S phases of the cell cycle. In patients with typical sleep schedules, this period may correspond to the hours when the patent is asleep (e.g., 1:00 AM to 6:00 AM).

In various embodiments, the process 700 may be repeated, e.g., repeated over several circadian cycles. In each repetition, the process may be modified to take into account, e.g., changes in the size and shape of the wound during the healing process.

In various embodiments, some of the steps in the above described method may be reordered or omitted. For example, in some embodiments, steps 206-207 regarding the application of mid-infrared light may be omitted. In other embodiments, steps 206-207 may be retained, but the near-infrared application of steps 204-205B may be omitted.

EXAMPLES

Human Keratinocyte and Fibroblast Circadian Tests

The following parameters illustrate the methods according to the disclosure as applied to Human Keratinocytes and Fibroblasts, to show that they indeed have circadian patterns that can be exploited.

Human keratinocytes are grown in dermal cell basal medium supplemented with 0.4% bovine pituitary extract, 0.5 ng/ml rh TGFalpha, 6 mM L-glutamine, 100 ng/ml hydrocortisone hemisuccinate, 5 µg/ml rh Insulin, 1 µM epinephrine, and 5 µg/ml apo-transferrin. The presence of hydrocortisone hemisuccinate might negatively impact the ability to measure circadian periods, as the presence of this steroid could constantly reset the cell periods.

Here we grew keratinocytes in complete media containing the normal 100 ng/ml hydrocortisone hemisuccinate compared to cells grown in media containing 50 ng/ml hydrocortisone hemisuccinate or in media without hydrocortisone hemisuccinate. To conduct this study cells were plated in triplicate in 6 well plates at a density of 55,000 cells per well (or 27,500 cells per ml) in each media condition. Cells were examined by Cedex analysis at 24, 48, and 72 hours following seeding.

Figure 10:
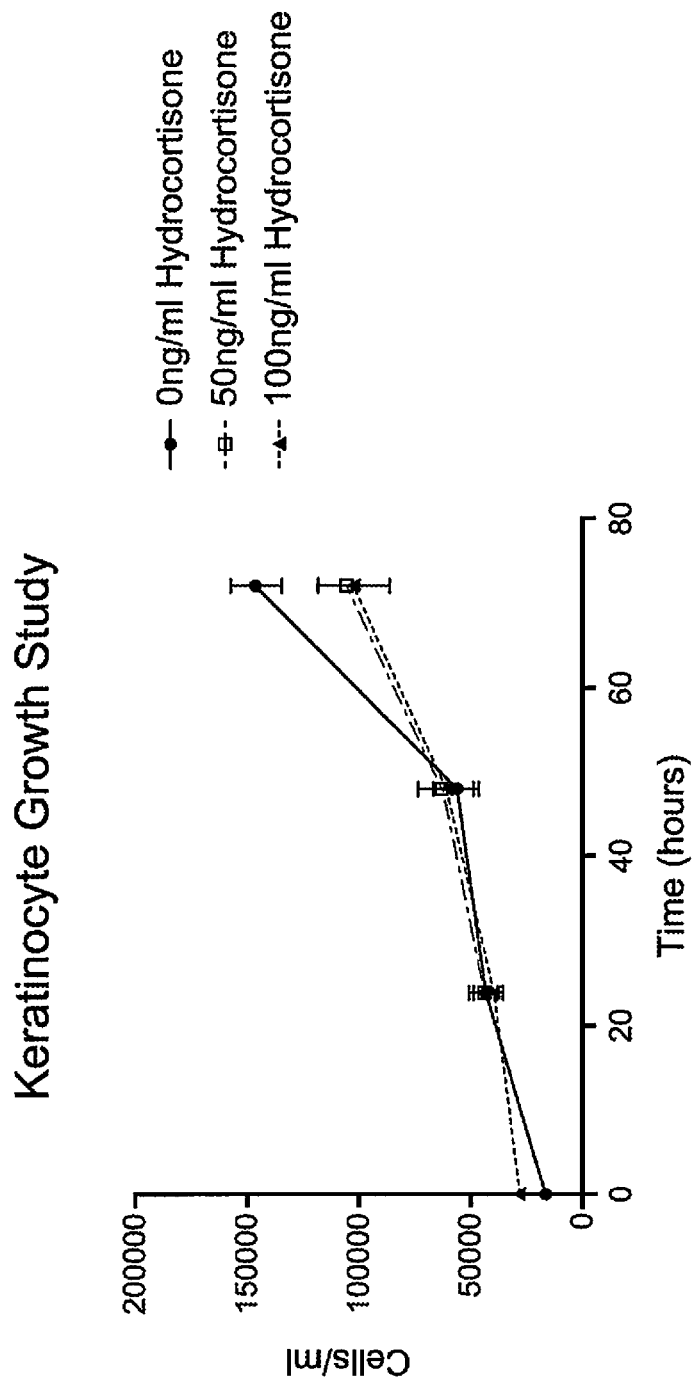
FIG. 10 illustrates a plot of keratinocyte growth (cells/ml) versus time (hours) for various hydrocortisone levels.

Results:

Cedex analysis of keratinocyte cell density at time of plating, 24, 48, and 72 hours following plating is shown in FIG. 11. Cell suspension was 2 ml total volume; 1 ml was read for Cedex analysis. Data is graphed in FIG. 10 as the as average+/−standard error.

As expected, excess cortical steroid caused chronodisruption of the cell cycle for the human keratinocytes studied.

Circadian Period Measurements of Human Keratinocytes and Fibroblasts

Human keratinocytes and skin fibroblasts were transfected with per2:luciferase or Bmal1:luciferase reporter constructs in triplicate on Dec. 13, 2012. The following day cells were synchronized with a 15 minute 100 nM dexamethasone treatment, transferred to the appropriate buffer containing luciferine and placed in an LM2400 luminometer which recorded luciferase activity by reading each culture dish for 1 minute every 15 minutes for 5 days. On Dec. 20, 2012 buffer was replaced with fresh buffer containing luciferine and recordings began again. Suprachiasmatic nucleus (SNC) and lung tissue explants were used as controls. The signal from human keratinocytes and skin fibroblasts was analyzed with WAVECLOCK analysis software and period measurements were calculated from the fibroblast samples. The keratinocyte samples did not function properly after transfection. Data for fibroblast circadian periods is about 24 hrs as expected and represented in FIG. 12.

Leptin Analysis for Irradiation of Human Adipocytes

The following parameters illustrate the methods according to the disclosure as applied to Human Adipocytes at thresholds well below thermal damage. Cultured human adipocytes were obtained from Zen-Bio Inc., North Carolina and used for in vitro experimentation. The adipocyte precursor cells (preadipocytes) were isolated from subcutaneous adipose tissue from elective surgery in healthy non-diabetic donors between 18 and 60 years old. The preadipocytes were isolated by centrifugal force after collagenase treatment, and then cultured as growing precursor cells. These cells were then differentiated into adipocytes using medium supplemented with adipogenic and lipogenic hormones. The process of differentiating preadipocytes to adipocytes is disclosed in U.S. Pat. No. 6,153,432.

Leptin Assay

Assessment of Leptin production and secretion from the human adipocytes was completed with a quantitative sandwich enzyme immunoassay technique. A monoclonal antibody specific for Leptin was pre-coated onto a microplate, and standards and samples were pipetted into the wells where any Leptin present was bound by an immobilized antibody. After washing away any unbound substances, an enzyme-linked monoclonal antibody specific for Leptin was added to the wells. Next, following a wash to remove any unbound antibody-enzyme reagent, a substrate solution was added to the wells and a color developed in proportion to the amount of Leptin bound in the initial step. Finally, the color development is stopped and the intensity (optical density) of the color was measured. The Leptin Assay kit was obtained from R&D Systems, Inc., 614 McKinley Place N.E. Minneapolis, Minn. 55413.

Cell Cultures for Experiments

All human adipocytes were plated into selected wells of 24-well tissue culture plates for selected NIMEL experiments at given dosimetry parameters. The plates were inoculated with isoproterenol immediately before irradiation to initiate biochemical lipolysis in all treatment and control wells.

Following Optical Treatments with a NIMEL Laser System, the directions were followed for the Zen-Bio Glycerol and Fatty Acid Assay kits described previously Equivalent assay studies and incubation times were performed for all NIMEL irradiation tests with Human Adipocyte Cells in the in vitro tests. Data in set in bold represent actual change from control (non-irradiated) samples.

Dosimetry Values for Optical Augmentation of Leptin Secretion

As summarized in Table I below, application of the single wavelength of about 930 nm with a dosimetry as shown in Table II caused approximately 43% augmentation of leptin pecretion in vitro during augmented lipolysis.

TABLE I

| Leptin Concentrations (pg/mL) - Calculations | | | | | |
|---|---|---|---|---|---|
| Plate | Dosimetry Parameters | T Ave | C Ave | NC Ave | % of Control |
| 1 | 930 nm, 0.5 W, 600 sec, 6 cm Dia | 23.6111 | 30.0000 | 33.3333 | 78.7% |
| 2 | 930 nm, 0.5 W, 900 sec, 6 cm Dia | 41.3889 | 41.1111 | 21.9444 | 100.7% |
| 3 | 930 nm, 0.5 W, 1200 sec, 6 cm Dia | 17.5000 | 12.2222 | 20.5556 | 143.2% |

TABLE II

| PLATE 3 DETAILED DOSIMETRY | | | | | |
|---|---|---|---|---|---|
| NIMEL OUTPUT POWER (W) 930 NM | BEAM SPOT 6 CM DIAMETER | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) |
| 0.5 W | 28.26 cm$^2$ | 20 min 1200 sec | 600 J | 20.4 J/cm$^2$ | 0.017 W/cm$^2$ |

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

As used herein the terms "light" and "optical" and related terms are to be understood to include electromagnetic radiation both within and outside of the visible spectrum, including, for example, ultraviolet and infrared radiation.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one."

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "including" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "or" as defined above. For example, when separating items in a list, "or" or "or" shall be interpreted as being inclusive, i.e., the inclusion of at least one, but also including more than one, of a number or list of elements, and, optionally, additional unlisted items. Only terms clearly indicated to the contrary, such as "only one of," or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In the claims, as well as in the specification above, all transitional phrases such as "including," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All definitions, as defined and used herein, should be understood to control over dictionary definitions, definitions in documents incorporated by reference, and/or ordinary meanings of the defined terms.

Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

REFERENCES

The following references are incorporated herein by reference in their entirety.
1) Al Ghamdi, Khalid M., Ashok Kumar, and Noura A. Moussa. "Low-level laser therapy: a useful technique for enhancing the proliferation of various cultured cells." Lasers in medical science 27.1 (2012): 237-249.
2) Peplow, Philip V., Tzu-Yun Chung, and G. David Baxter. "Laser photobiomodulation of proliferation of cells in culture: a review of human and animal studies." Photomedicine and Laser Surgery 28.S1 (2010): 3-40.
3) Nteleki, Bahle, and Nicolette Nadene Houreld. "The use of phototherapy in the treatment of diabetic ulcers." Journal of Endocrinology, Metabolism and Diabetes of South Africa 17.3 (2012): 128-132.
4) Huang, Ying-Ying, et al. "Biphasic Dose Response in Low Level Light Therapy."Dose-Response 7.4 (2009): 358
5) Duffy J F, Czeisler C A. Effect of light on human circadian physiology. Sleep Med Clin 4: 165-177, 2009.
6) Bartness T J, Song C K, Demas G E. SCN efferents to peripheral tissues: implications for biological rhythms. J Biol Rhythms 16: 196-204, 2001.
7) Sukumaran S, Almon R R, DuBois D C, Jusko W J. Circadian rhythms in gene expression: relationship to physiology, disease, drug disposition and drug action. Adv Drug Deliv Rev 62: 904-917, 2010.
8) Brown, Steven A., et al. "The period length of fibroblast circadian gene expression varies widely among human individuals." PLoS biology 3.10 (2005): e338.
9) Sandu, Cristina, et al. "Human skin keratinocytes, melanocytes, and fibroblasts contain distinct circadian clock machineries." Cellular and Molecular Life Sciences (2012): 1-11.
10) Lévi, Francis, et al. "Circadian timing in cancer treatments." Annual review of pharmacology and toxicology 50 (2010): 377-421.
11) Sancar, Aziz, et al. "Circadian clock control of the cellular response to DNA damage." FEBS letters 584.12 (2010): 2618-2625.
12) Gachon, Frédéric, and Dmitri Firsov. "The role of circadian timing system on drug metabolism and detoxification." Expert opinion on drug metabolism & toxicology 7.2 (2011): 147-158.
13) Ratner S, Jasti R K, Heppner G H (1988) Motility of murine lymphocytes during transit through cell cycle. Analysis by a new in vitro assay. J Immunol 140:583-588
14) Iwasaki T, et al (1995)Cell cycle-dependent invasion in vitro by rat ascites hepatoma cells. Int J Cancer 63: 282-287
15) Walmod P S, Hartmann-Petersen R, Prag S, Lepekhin E L, R€opke C, Berezin V, Bock E (2004)Cell-cycle-dependent regulation of cell motility and determination of the role of Racl. Exp Cell Res 295:407-420
16) Wang N, Tytell J D, Ingber D E. Mechanotransduction at a distance: mechanically coupling the extracellular matrix with the nucleus. Nature Reviews Molecular Cell Biology 2009; 10:75-82.

17) Wang J H, Thampatty B P. Mechanobiology of adult and stem cells. International Review of Cellular and Molecular Biology 2008; 271:301-46.
18) Knies Y, Bernd A, Kaufmann R, Bereiter-Hahn J, Kippenberger S. Mechanical stretch induces clustering of beta1-integrins and facilitates adhesion. Experimental Dermatology 2006; 15:347-55.
19) Reichelt J. Mechanotransduction of keratinocytes in culture and in the epidermis. European Journal of Cell Biology 2007; 86:807-16.
20) Takei T, Rivas-Gotz C, Delling C A, Koo J T, Mills I, McCarthy T L, et al. Effect of strain on human keratinocytes in vitro. Journal of Cellular Physiology 1997; 173: 64-72. [25] Reno F, Traina V, Cannas M. Mechanical stretching modulates growth direction and MMP-9 release in human keratinocyte monolayer. Cell Adhesion and Migration 2009; 3:239-42.
21) Perozo E, Cortes D M, Sompornpisut P, et al. Open channel structure of MscL and the gating mechanism of mechanosensitive channels. Nature 2002; 418:942-8.
22) Perozo E, Kloda A, Cortes D M, et al. Physical principles underlying the transduction of bilayer deformation forces during mechanosensitive channel gating. Nat Struct Biol 2002; 9:696-703.
23) Ingber D E. Cellular mechanotransduction: putting all the pieces together again. Faseb J 2006; 20:811-27.
24) Ingber D E. Tensegrity: the architectural basis of cellular mechanotransduction. Annu Rev Physiol 1997; 59:575-99.
25) Orr A W, Helmke B P, Blackman B R, et al. Mechanisms of mechanotransduction. Dev Cell 2006; 10:11-2.
26) Gov, Nir S., and Ajay Gopinathan. "Dynamics of membranes driven by actin polymerization." *Biophysical journal* 90.2 (2006): 454-469.
27) Gov, N. "Membrane undulations driven by force fluctuations of active proteins."*Physical review letters* 93.26 (2004): 268104.
28) Gov, N., and S. A. Safran. "Red blood cell shape and fluctuations: cytoskeleton confinement and ATP activity." *Journal of Biological Physics* 31.3 (2005): 453-464.
29) Lin, Lawrence C-L., Nir Gov, and Frank L H Brown. "Nonequilibrium membrane fluctuations driven by active proteins." *The Journal of chemical physics* 124 (2006): 074903.
30) Krol, A. Yu, et al. "Local mechanical oscillations of the cell surface within the range 0.2-30 Hz." European biophysics journal 19.2 (1990): 93-99.
31) Sheetz M P, Felsenfeld D, Galbraith C G, Choquet D: Cell migration as a five-step cycle. Biochem Soc Symp 1999, 65:233-243
32) Alt W, Brosteanu O, Hinz B, Kaiser H W: Patterns of spontaneous motility in videomicrographs of human epidermal keratinocytes (HEK). Biochem Cell Biol 1995, 73:441-459.
33) Giannone G, Dubin-Thaler B J, Rossier O, Cai Y, Chaga O, Jiang G, Beaver W, Do"bereiner H-G, Freund Y, Borisy G et al.: Lamellipodial actin mechanically links myosin activity with adhesion-site formation. Cell 2007, 128:561-575.
34) Giannone G, Dubin-Thaler B J, Do"bereiner H-G, Kieffer N, Bresnick A R, Sheetz M P: Periodic lamellipodial contractions correlate with rearward actin waves. Cell 2004, 116:431-443.
35) Alt, Wolfgang, and Micah Dembo. "Cytoplasm dynamics and cell motion: two-phase flow models." Mathematical biosciences 156.1 (1999): 207-228.
36) Driscoll, Meghan K., et al. "Cell shape dynamics: from waves to migration." PLoS Computational Biology 8.3 (2012): e1002392.
37) Albrecht-Buehler, Guenter. "Surface extensions of 3T3 cells towards distant infrared light sources." *The Journal of cell biology* 114.3 (1991): 493-502.
38) Albrecht-Buehler, Guenter. "Is cytoplasm intelligent too?." *Cell and muscle motility* 6 (1985): 1.
39) Tsai M A, Waugh R E, Keng P C (1996) Cell cycle-dependence of HL-60 cell deformability. Biophys J 70:2023-2029
40) Giet O, Van Bockstaele D R, Di Stefano I, Huygen S, Greimers R, Beguin Y, Gothot A (2002) Increased binding and defective migration across fibronectin of cycling hematopoietic progenitor cells. Blood 99:2023-2031
41) Sinha M K, Sturis J, Ohannesian J, et al. 1996 Ultradian oscillations of leptin secretion in humans. Biochem Biophysical Res Commun 228:733-738
42) Licinio J, Mantzoros C, NegraoAB, et al. 1997 Human leptin levels are pulsatile and inversely related to pituitary-adrenal function. Nat Med 3:575-579
43) Ahmad, Aftab M., et al. "Circadian and ultradian rhythm and leptin pulsatility in adult GH deficiency: effects of GH replacement." Journal of Clinical Endocrinology & Metabolism 86.8 (2001): 3499-3506.
44) Frank S, Stellmeyer B, Kampfer H, Kolb N, Pfeilschifter J (2000) Leptin enhances wound reepithe-lialization and constitutes a direct function of leptin in skin repair. J Clin Invest 106:501-509
45) Murad A, Nath A K, Cha S T, Demir E, Flores-Riveros J, Sierra-Honigmann M R (2003) Leptin is an autocrine/paracrine regulator of wound healing. FASEB J 17:1895-1897
46) Tomonobu Ezure* and Satoshi Amano, Adiponectin and leptin up-regulate extracellular matrix production by dermal fibroblasts. BioFactors 31 (2007) 229-236 229
47) A. Glasoe et al, Expression of Leptin (Ob) and Leptin Receptor (Ob-R) in Human Fibroblasts: Regulation of Leptin Secretion by Insulin. J Clin Endocrinol Metab 86: 4472-4479, 2001)
48) Peura, M. et al, Improved skin wound epithelialization by topical delivery of soluble factors from fibroblast aggregates. Burns. 2012 June; 38(4):541-50. Epub 2011 Nov. 22
49) Hutson, M. Shane, and Glenn S. Edwards. "Advances in the physical understanding of laser surgery at 6.45 microns." *Intl. Free Electron Laser Conf.* 2004.
50) Gelse, K., E. Pöschl, and T. Aigner. "Collagens—structure, function, and biosynthesis." *Advanced drug delivery reviews* 55.12 (2003): 1531-1546.
51) Serebryakov, V. A., et al. "Medical applications of mid-IR lasers. Problems and prospects." *Journal of Optical Technology* 77.1 (2010): 6-17.
52) Converse, I. V., et al. "Comparison of wound healing using the CO2 laser at 10.6 µm and 9.55 µm." The Laryngoscope 111.7 (2001): 1231-1236.
53) Toyokawa H, et al., Promotove effects of far-infrared ray on full-thickness skin wound healing in rats, Soc Experimental Biology and Medicine, 724-729 (2004).

What is claimed is:
1. A method of providing photo-chrono-therapy to a wound site in a human or animal subject, the method comprising:
determining or receiving subject circadian and/or ultradian cycle information indicative of a biological rhythm(s) of the subject; and based on the subject cycle information, delivering a photo-chrono-dose of infrared treatment light to the wound site with wavelengths within at least one infrared wavelength range and having a dosimetry configured to promote healing at the wound site.

2. The method of claim 1, wherein
the subject cycle information comprises circadian information indicative of a circadian rhythm of the subject, and
delivering the photo-chrono-dose comprises delivering the treatment light at a time corresponding to one or more selected phases in a cell-cycle of the subject based on the circadian information.

3. The method of claim 2, wherein the one or more selected phases comprise a G1 or early S-phase of the cell-cycle.

4. The method of claim 1, wherein the wound site comprises an internal peripheral portion and an external peripheral portion each having a wound margin and a central portion, and wherein delivering a photo-chrono-dose of infrared treatment light to the wound site comprises preferentially delivering light to either or both of the peripheral portions of the wound singly or simultaneously.

5. The method of claim 4, further comprising stimulating migration of eukaryotic cells from the peripheral portion of the wound site to the central portion of the wound site.

6. The method of claim 5, wherein the eukaryotic cells comprise at least one of fibroblasts and keratinocytes.

7. The method of claim 6, wherein stimulating migration of eukaryotic cells comprises generating spatio-temporal photo-taxis in the eukaryotic cells.

8. The method of claim 7, wherein generating spatio-temporal photo-taxis in the eukaryotic cells comprises causing optically mediated mechanotransduction at cell membranes to stimulate directed lamellopod or pseudopod creation in the cells.

9. The method of claim 8, wherein the optically mediated mechanotransduction causes forces at the cell membrane that reinforce endogenous membrane waves in the cells.

10. The method of claim 9, wherein preferentially delivering light to the internal or external peripheral portion comprises delivering the light with a substantially annular spatial distribution.

11. The method of claim 10, the light with a substantially annular spatial distribution comprises delivering the light as a ring of spots at the wound cite.

12. The method of claim 1, wherein the subject cycle information comprises ultradian information indicative of an ultradian rhythm of the subject, and further comprising modulating the treatment light delivered to the wound site based on the ultradian information.

13. The method of claim 12, wherein the ultradian information comprises information indicative of a pulse or heartbeat in the subject.

14. The method of claim 13, further comprising receiving at least one sensor signal indicative of the ultradian information.

15. The method of claim 14, wherein the sensor signal comprises a pulse oximeter signal or an electrocardiogram signal.

16. The method of claim 1, wherein delivering the photo-chrono-dose of infrared treatment light comprises:
generating near-infrared optical radiation with wavelengths within a first wavelength range of 850 nm to 900 nm or a second wavelength range of 910 nm to 950 nm; and
delivering the near-infrared optical radiation to the wound site with a power density at the treatment sight in the range of 0.015-1.0 W/cm^2 and an energy density in the range of 0.5-3500 J/cm^2.

17. The method of claim 16, wherein the near-infrared optical radiation comprises radiation in the first and second wavelength ranges.

18. The method of claim 16, comprising:
stimulating collagen synthesis at the wound site by delivering mid-infrared optical radiation to the wound site;
wherein delivering mid-infrared optical radiation to the wound site comprises:
generating mid-infrared optical radiation substantially in a third wavelength range of 6.35 microns to 6.55 microns; and
delivering the mid-infrared optical radiation to the wound site with a power density at the treatment sight in the range of 0.01-1.0 W/cm^2 and an energy density in the range of 0.5-3500 J/cm^2.

19. The method of claim 1, further comprising applying the near infrared optical radiation to stimulate leptin production from adipose tissue in the external periphery of the wound site.

20. The method of claim 1, further comprising intentionally creating a wound at the wound site.

* * * * *